(12) United States Patent
Donavon et al.

(10) Patent No.: US 12,080,416 B2
(45) Date of Patent: Sep. 3, 2024

(54) SYSTEMS AND METHODS FOR ANIMAL HEALTH MONITORING

(71) Applicant: Société des Produits Nestlé S.A., Vevey (CH)

(72) Inventors: Mark Alan Donavon, Troy, IL (US); Natalie Langenfeld-McCoy, Bethalto, IL (US); Ragen Trudelle-Schwarz McGowan, Saint Joseph, MO (US); Helber Dussan, Saint Louis, MO (US); Mani Bharath Kamaraj, Coimbatore (IN); Vignesh Vijayarajan, Chennai (IN); Venkatakrishnan Govindarajan, Chennai (IN); Ajay Singh, Madhya Pradesh (IN); Sarath Malipeddi, Andhra Pradesh (IN); Abhishek Sai Nasanuru, Tirupati (IN); Ayushi Krishnan, Bihar (IN); Dwarakanath Raghavendra Ravi, Chennai (IN); Daniel James Sherwood, Cambridge (GB); Russell Stewart Maguire, Cambridge (GB); Jack William James Stone, Cambridge (GB); Georgina Elizabeth Mary Logan, Cambridge (GB); Tomoko Hatori, Cambridge (GB); Peter Michael Haubrick, Cambridge (GB); Wendela Sophie Schim van der Loeff, Cambridge (GB)

(73) Assignee: Société des Produits Nestlé S.A., Vevey (CH)

( * ) Notice: Subject to any disclaimer, the term of this patent is extended or adjusted under 35 U.S.C. 154(b) by 189 days.

(21) Appl. No.: 17/896,399

(22) Filed: Aug. 26, 2022

(65) Prior Publication Data
US 2023/0068528 A1    Mar. 2, 2023

Related U.S. Application Data

(60) Provisional application No. 63/237,664, filed on Aug. 27, 2021.

(51) Int. Cl.
*G16H 40/63* (2018.01)
(52) U.S. Cl.
CPC .................... *G16H 40/63* (2018.01)
(58) Field of Classification Search
CPC ..................................... G16H 40/63
See application file for complete search history.

(56) References Cited

U.S. PATENT DOCUMENTS

| 8,437,980 B2 * | 5/2013 | Yuen | A61B 5/4815 |
| | | | 702/160 |
| 8,683,952 B2 * | 4/2014 | Miller | A01K 1/011 |
| | | | 119/165 |

(Continued)

OTHER PUBLICATIONS

Mcgowan, The ins and outs of the litter box: A detailed ethogram of cat elimination behavior in two contrasting environments, Applied Animal Behaviour Science, 2017, pp. 1-12.

(Continued)

*Primary Examiner* — Michael I Ezewoko

(57) ABSTRACT

The present disclosure provides systems and methods for animal health monitoring. Load data can be obtained from an animal monitoring device including three or more load sensors associated with a platform carrying contained litter thereabove, wherein individual load sensors of the three or more load sensors are separated from one another and receive pressure input from the platform independent of one another, wherein the three or more load sensors individually sample loads at from 2.5 Hz to 110 Hz. An animal behavior property associated with the animal can be recognized if it is determined based on load data that the interaction with the contained litter was due to the animal interaction with the (Continued)

contained litter. The animal behavior property can be classified into an animal classified event using a machine learning classifier.

46 Claims, 26 Drawing Sheets

(56) References Cited

U.S. PATENT DOCUMENTS

| | | | | |
|---|---|---|---|---|
| 8,704,668 B1* | 4/2014 | Darrell | A01K 29/005 |
| | | | 340/573.3 |
| 8,797,166 B2* | 8/2014 | Triener | A01K 5/0114 |
| | | | 340/573.3 |
| 9,149,022 B2* | 10/2015 | Triener | A01K 5/0114 |
| 9,420,766 B2* | 8/2016 | Triener | G01G 17/08 |
| 9,510,566 B2* | 12/2016 | Pantazes | A01K 29/005 |
| 9,770,013 B2* | 9/2017 | Kim | A01K 11/00 |
| 10,104,871 B2* | 10/2018 | Triener | G16Z 99/00 |
| 10,149,617 B2* | 12/2018 | Couse | A61B 5/7275 |
| 10,463,023 B2* | 11/2019 | Perez-Camargo | A61B 5/4255 |
| 10,729,097 B2* | 8/2020 | Kaneko | A01K 29/00 |
| 10,791,716 B2* | 10/2020 | Triener | A01K 7/00 |
| 10,922,995 B2 | 2/2021 | Donavon | |
| 10,959,409 B2* | 3/2021 | Triener | A01K 5/0114 |
| 11,039,603 B2* | 6/2021 | Triener | G16Z 99/00 |
| 11,249,544 B2* | 2/2022 | Sicconi | G08B 3/1016 |
| 11,252,931 B2 | 2/2022 | Huang | |
| 11,284,599 B2* | 3/2022 | Hori | A01K 1/01 |
| 11,514,766 B1* | 11/2022 | McDaniel | G08B 13/2485 |
| 11,666,037 B2* | 6/2023 | Wernimont | A01K 29/005 |
| | | | 600/595 |
| 2012/0299731 A1* | 11/2012 | Triener | G16Z 99/00 |
| | | | 702/19 |
| 2013/0014706 A1* | 1/2013 | Menkes | A01K 27/001 |
| | | | 119/859 |
| 2014/0331942 A1* | 11/2014 | Sarazyn | A01K 29/005 |
| | | | 119/859 |
| 2014/0347184 A1* | 11/2014 | Triener | G16Z 99/00 |
| | | | 340/573.1 |
| 2015/0039239 A1* | 2/2015 | Shuler | G16H 40/67 |
| | | | 702/19 |
| 2016/0012748 A1* | 1/2016 | Donavon | G09B 19/0092 |
| | | | 434/225 |
| 2016/0198960 A1* | 7/2016 | Menkes | A01K 27/001 |
| | | | 119/859 |
| 2016/0262356 A1* | 9/2016 | Perez-Camargo | A61B 5/4255 |
| 2016/0310012 A1* | 10/2016 | Mankowski | A01K 29/005 |
| 2016/0360733 A1* | 12/2016 | Triener | G01G 21/22 |
| 2017/0000090 A1* | 1/2017 | Hall | A01K 29/005 |
| 2017/0272843 A1* | 9/2017 | Dror | A01K 29/005 |
| 2017/0372631 A1* | 12/2017 | Meggs | G06F 16/2282 |
| 2018/0359987 A1* | 12/2018 | Kaneko | A01K 1/0114 |
| 2019/0029226 A1* | 1/2019 | Triener | A01K 31/12 |
| 2020/0205381 A1* | 7/2020 | Wernimont | A01K 29/005 |
| 2020/0236897 A1* | 7/2020 | Hori | A01K 29/005 |
| 2020/0390068 A1* | 12/2020 | Triener | G01G 17/08 |
| 2020/0396965 A1* | 12/2020 | Triener | G16Z 99/00 |
| 2023/0061071 A1* | 3/2023 | Donavon | A01K 29/005 |

OTHER PUBLICATIONS

International Search Report and Written Opinion to PCT/IB2022/058016 dated Nov. 8, 2022.

* cited by examiner

1100

| Weight Difference | Number of Cats | Number of Cat Pairs | Type of Model | | |
|---|---|---|---|---|---|
| | | | Feature Based | Location Based | Hybrid Model |
| High Weight Overlap | 2 | 75 | 76% | 70% | 76% |
| | 3 | 240 | 72% | 63% | 72% |
| | 4 | 240 | 61% | 53% | 61% |
| Medium Weight Overlap | 2 | 59 | 88% | 90% | 90% |
| | 3 | 80 | 84% | 92% | 92% |
| | 4 | 80 | 81% | 92% | 92% |
| Low Weight Overlap | 2 | 362 | 96% | 98% | 98% |
| | 3 | 320 | 88% | 97% | 97% |
| | 4 | 280 | 84% | 96% | 96% |

FIG. 11

1400 obtaining load data from an animal monitoring device including three or more load sensors associated with a platform carrying contained litter thereabove, wherein individual load sensors of the three or more load sensors are separated from one another and receive pressure input from the platform independent of one another — 1410 recognizing an animal behavior property associated with the animal if determined based on load data that the interaction with the contained litter was due to the animal interaction with the contained litter — 1412 classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations when they occur — 1414

FIG. 14

SYSTEMS AND METHODS FOR ANIMAL HEALTH MONITORING

The present application claims the benefit of U.S. Provisional Patent Application No. 63/237,664, filed on Aug. 27, 2021, which is incorporated in its entirety by reference.

BACKGROUND

Litter boxes are used by cats for elimination of urine and fecal matter. A litter box contains a layer of cat litter that receives the urine and fecal matter. The pet litter comprises an absorbent and/or adsorbent material which can be non-clumping or clumping. Visual indicators related to litter box use may provide information about a cat's health; for example, the onset of physical, behavioral, or mental health issues. Unfortunately, these symptoms may only occur in mid- to late-stages of a disease or health issue and often do not provide enough information for correct intervention. Moreover, pet owners often lack the animal behavioral knowledge to associate litter box use with health issues.

There have been some efforts to track litter box activity as a means to assess a cat's health. For example, cameras, video recording devices, and/or scales have been used to capture a cat's litter box activity. While these devices may be helpful in tracking some basic information about a cat's behavior, these devices typically provide one-dimensional information, may require a qualified behaviorist to interpret, and/or may lack the ability to provide good data on more subtle and/or non-visual clues.

BRIEF DESCRIPTION OF THE FIGURES

FIG. 11 illustrates examples of the performance of various classification models in accordance with the present disclosure.

FIGS. 12-14 illustrate flowcharts of example methods for monitoring the health of an animal in accordance with the present disclosure.

DETAILED DESCRIPTION

Figure 1A:
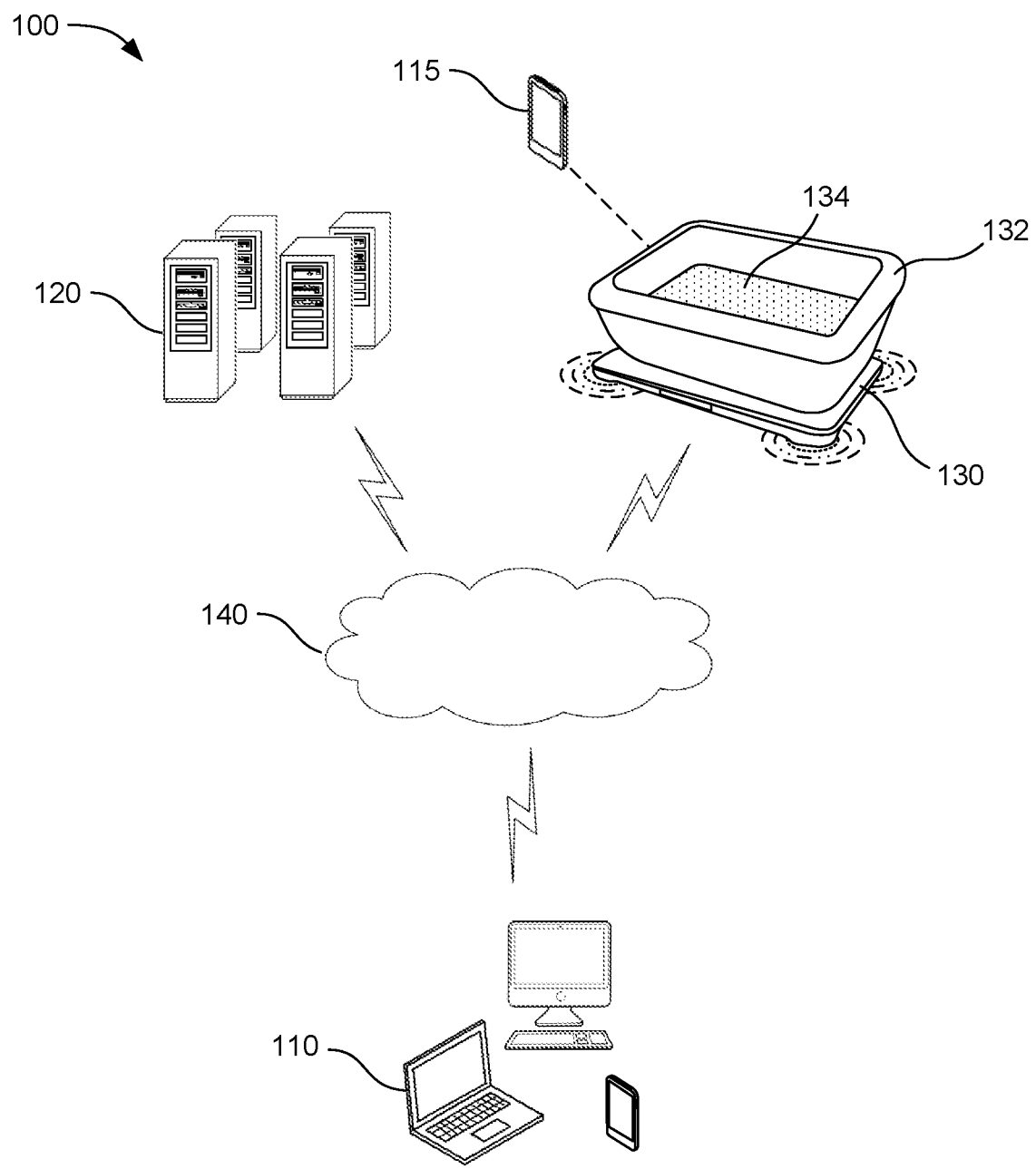
FIGS. 1A-1E schematically illustrate example animal health monitoring systems in accordance with the present disclosure.

The present disclosure relates to the field of animal health and behavior monitoring, and more particularly, devices, systems, methods, and computer program products for determining, monitoring, processing, recording, and transferring over a network of various physiological and behavioral parameters of animals.

In accordance with examples of the present disclosure, a method of monitoring the health of an animal under the control of at least one processor is disclosed. The method can include obtaining load data from an animal monitoring device including three or more load sensors associated with a platform carrying contained litter thereabove, wherein individual load sensors of the three or more load sensors are separated from one another and receive pressure input from the platform independent of one another, wherein the three or more load sensors individually sample loads at from 2.5 Hz to 110 Hz. The method can further include recognizing an animal behavior property associated with the animal if it is determined based on load data that the interaction with the contained litter was due to the animal interaction with the contained litter. The method can further include classifying the animal behavior property into an animal classified event using a machine learning classifier.

In another example, the present disclosure provides an animal monitoring system including an animal monitoring device. The animal monitoring device can include a platform configured to carry contained litter thereabove. The device can further include three or more load sensors associated with the platform, wherein individual load sensors of the three or more load sensors are separated from one another and receive pressure input from the platform independent of one another, wherein the three or more load sensors individually have a sampling rate in a range of 2.5 Hz to 110 Hz. The device can further include a data communicator configured to independently communicate the load data from the three or more load sensors.

In another example, the present disclosure provides a method of monitoring the health of an animal under the control of at least one processor. The method can include obtaining load data from an animal monitoring device including three or more load sensors associated with a platform carrying contained litter thereabove, wherein individual load sensors of the three or more load sensors are separated from one another and receive pressure input from the platform independent of one another. The method can further include recognizing an animal behavior property associated with the animal if it is determined based on load data that the interaction with the contained litter was due to the animal interaction with the contained litter. The method can further include classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations when they occur.

In another example, the present disclosure provides an animal monitoring system including an animal monitoring device. The animal monitoring device can include a platform configured to carry contained litter thereabove. The animal monitoring device can further include three or more load sensors associated with the platform, wherein individual load sensors of the three or more load sensors are separated from one another and receive pressure input from the platform independent of one another. The animal monitoring device can further include a data communicator configured to independently communicate the load data from the three or more load sensors. The animal monitoring device can further include a processor and memory storing instructions that, when executed by the processor, comprise obtaining load data independently from the three or more load sensors. The instructions further comprise recognizing an animal behavior property associated with the animal if it is determined based on load data that an interaction with the platform was due to an animal interaction. The instructions further comprise classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations when they occur.

In another example, the present disclosure provides a non-transitory machine readable storage medium having instructions embodied thereon, the instructions which, when executed, cause a processor to perform a method of monitoring the health of an animal. The method can include obtaining load data from an animal monitoring device including three or more load sensors associated with a platform carrying contained litter thereabove, wherein individual load sensors of the three or more load sensors are separated from one another and receive pressure input from the platform independent of one another. The method can further include recognizing an animal behavior property associated with the animal if it is determined based on load data that the interaction with the contained litter was due to the animal interaction with the contained litter. The method can further include classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations when they occur.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

Definitions

As used herein, "about," "approximately" and "substantially" are understood to refer to numbers in a range of numerals, for example the range of −10% to +10% of the referenced number, −5% to +5% of the referenced number, −1% to +1% of the referenced number, or −0.1% to +0.1% of the referenced number. All numerical ranges herein should be understood to include all integers, whole numbers or fractions within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

The terms "pet" and "animal" are used synonymously herein and mean any animal which can use a litter box, non-limiting examples of which include a cat, a dog, a rat, a ferret, a hamster, a rabbit, an iguana, a pig or a bird. The pet can be any suitable animal, and the present disclosure is not limited to a specific pet animal. The term "elimination" means urination and/or defecation by a pet.

As used herein, the term "litter" means any substance that can absorb animal urine and/or decrease odor from animal urine and/or feces. A "clumping litter" forms aggregates in the presence of moisture, where the aggregates are distinct from the other litter in the litter box. A "clumping agent" binds adjacent particles when wetted. A "non-clumping litter" does not form distinct aggregates.

The term "litter box" means any apparatus that can hold pet litter, for example a container with a bottom wall and one or more side walls, and/or any apparatus configured for litter to be positioned thereon, for example a mat or a grate. As a non-limiting example, a litter box may be a rectangular box having side walls that have a height of at least about six inches.

Animal Health Monitoring

In accordance with the present disclosure, systems and methods for animal health monitoring can be based on locations where an animal typically eliminates. For example, animal health monitoring systems for cats can be typically placed under the cat's litter box. This can be particularly beneficial as this configuration allows pet owners to use their existing cat litter box and cat litter, minimizing any risk of cat elimination behavior issues that can occur when litter boxes are changed. In other examples, however, the systems and methods can likewise be carried out using a new litter box or even a litter box integrated or designed/shaped for use with the platforms and load sensors of the present disclosure. In further detail, although the systems and techniques described herein are described with respect to cats and cat behaviors, it should be noted that the systems and techniques described herein can be used to monitor the behaviors of any animal.

In examples of the present disclosure, animal health monitoring systems may include one or more load sensors. The load sensors can monitor the distribution of the weight of the animal within the animal health monitoring system and the time the animal is located within the area monitored by the animal health monitoring system. For example, the load sensor data can be used to track a cat's movement patterns in the litter box, identify non-cat interactions with the box, identify individual cats in a multi-cat scenario, identify litter box maintenance events, and/or predict a number of insights unique to each cat/litter box event. Based on this information, a variety of events can be determined that describe the animal's behavior. For example, a determination can be made if the load sensor data is derived from cat behaviors and/or a person interacting with the litter box. If the behaviors are associated with a cat, a determination can be made if the cat is interacting with the inside or outside of the litter box. If the cat is inside the litter box, the identity of the cat and/or the cat's activity (urinating, defecating, etc.) can be determined. If the cat is outside the litter box, a variety of behaviors (e.g., rubbing the box, balancing on the edge of the box, etc.) can be determined. If the behaviors are associated with a person, it can be determined if the person is scooping the litter, adding litter, interacting with the litter box, interacting with the animal health monitoring system, and the like.

The animal health monitoring system can automatically track visit frequency, visit type (e.g., elimination vs. non-elimination), and/or animal weight across multiple visits. This historical information can be used to monitor animal weight, litter box visit frequencies, and/or elimination behaviors over time. This information, optionally combined with a variety of other data regarding the animal (e.g., age/life stage, sex, reproductive status, body condition, rate-of-change in weight or behavior, and the like) can be used to identify when changes occur and/or predict potential health or behavioral conditions affecting the animal.

In addition to identifying animal behaviors, the animal health monitoring system can advantageously provide early indicators of potential health conditions including, but not limited to, physical, behavioral and mental health of an animal. Examples of physical health include but are not limited to renal health, urinary health, metabolic health and digestive health. More specifically, animal diseases that may be correlated with weight and behavioral data obtained from use of the animal health monitoring system include but are not limited to feline lower urinary tract disease, diabetes, irritable bowel syndrome, feline idiopathic cystitis, bladder stones, bladder crystals, arthritis, hyperthyroidism, diabetes, and/or a variety of other diseases potentially affecting the animal. Examples of behavioral health include, but are not limited to, out of the box elimination and/or cat social dynamics in a multi-cat household. Examples of mental health include, but are not limited to, anxiety, stress and cognitive decline. Based on these potential health conditions, proactive notifications can be provided to the animal's owner and/or veterinarian for further diagnosis and treatment.

The animal health monitoring systems and techniques described herein may provide a variety of benefits over existing systems (though it is noted that the systems and methods described herein can be used in some instances in conjunction with some of these existing monitoring systems). Existing monitoring systems typically rely on microchips implanted into the animals, RFID-enabled collars, and/or visual image recognition to identify individual cats. These systems can be very invasive (e.g., veterinarian intervention to implant a microchip into a specific location in the animal), prone to failure (e.g., microchips can migrate to another location within the animal and be difficult to locate, RFID collars can wear out, be lost, and/or need frequent battery replacement/recharging, cameras can require precise positioning and maintenance, and the like), and/or very disruptive to the animal's typical behaviors. For example, the presence and/or audible noise of a camera system or human observer can discourage certain cats from using their litter box in a manner that they might otherwise normally be inclined. Further, some existing systems require specific materials (such as specific litter types) to be used.

Animal health monitoring systems in accordance with the present disclosure address some of limitations of existing systems, particularly in instances where some of these other systems interfere with the animal's normal behavior. The animal health monitoring systems of the present disclosure can, for example, identify and track animals without relying on external identification, such as microchips or RFID collars. Furthermore, in some examples, the animal health monitoring systems described herein can identify the animal and its behavior without relying on image or video information, thereby avoiding the usage of cameras or human observers that can affect the animal's typical behaviors. For example, the animal health monitoring system provided herein can identify an individual animal from a plurality of animals. In other words the animal health monitoring system can differentiate between and provide independent health monitoring for each cat in a multiple cat household. In a number of embodiments, animal health monitoring systems include more than one load sensor, allowing for more detailed information regarding the animal and its movement patterns to be generated as compared to existing systems. To illustrate, the sensors utilized in the animal health monitoring systems are located in positions that do not disrupt the cat's natural behavior. The animal health monitoring systems are designed with a low profile to accommodate even very young or senior cats since these cats can have difficulty entering a box with a higher profile. Further, the animal health monitoring systems can utilize a cat's existing litter box and can be used with any type of litter (e.g. clumping or non-clumping litter), thereby avoiding elimination behavior issues that can occur if the litter type is switched. The animal health monitoring systems can utilize battery power or main power, allowing for use in areas where there are no outlets, eliminating the power cord which presents a tripping hazard or allowing for cats who are known cord chewers.

Turning now to the drawings, FIG. 1A schematically illustrates an animal health monitoring system 100. The animal health monitoring system can include client devices 110, analysis server systems 120, and/or an animal monitoring device 100 in communication via network 140. In this example, a litter box or container 132 that contains litter 134 rests on top of the animal monitoring device. The litter may be cat litter. In some examples, the analysis server systems may be implemented using a single server. In other aspects, the analysis server systems can be implemented using a plurality of servers. In still other examples, client devices can be interactive with and implemented utilizing the analysis server systems and vice versa.

Client devices 110 can include, for example, desktop computers, laptop computers, smartphones, tablets, and/or any other user interface suitable for communicating with the animal monitoring devices. Client devices can obtain a variety of data from one or more animal monitoring devices 130, provide data and insights regarding one or more animals via one or more software applications, and/or provide data and/or insights to the analysis server systems 120 as described herein. The software applications can provide data regarding animal weight and behavior, track changes in the data over time, and/or provide predictive health information regarding the animals as described herein. In some embodiments, the software applications obtain data from the analysis server systems for processing and/or display.

Analysis server systems 120 can obtain data from a variety of client devices 110 and/or animal monitoring devices 130 as described herein. The analysis server systems can provide data and insights regarding one or more animals and or transmit data and/or insights to the client devices as described herein. These insights can include, but are not limited to, insights regarding animal weight and behavior, changes in the data over time, and/or predictive health information regarding the animals as described herein. In a number of embodiments, the analysis server systems obtain data from multiple client devices and/or animal monitoring devices, identify cohorts of animals within the obtained data based on one or more characteristics of the animals, and determine insights for the cohorts of animals. The insights for a cohort of animals can be used to provide recommendations for a particular animal that has characteristics in common with the characteristics of the cohort. In many embodiments, the analysis server systems provide a portal (e.g., a web site) for vets to access information regarding particular animals.

Animal monitoring devices 130 can obtain data regarding the interactions of animals and/or people with the animal monitoring device. In some embodiments, the animal monitoring devices include a waste elimination area (e.g. a litter box) and one or more load sensors. In several embodiments, the load sensors include motion detection devices, accelerometers, weight detection devices, and the like. The load sensors can be located in a position that does not disrupt the cat's natural behavior. The load sensors can automatically detect a presence of the cat in the litter box and/or automatically measure a characteristic of the cat when it is in the litter box or after it has left the litter box. Additionally, the load sensors can be positioned to track an animal's movements within the litter box. The data captured using the load sensors can be used to determine animal elimination behaviors, behaviors other than elimination behaviors that may occur inside or outside of the litter box (e.g., cats rubbing the litter box), and/or other environmental activities as described herein. The animal monitoring devices can transmit data to the client devices 110 and/or analysis server systems 120 for processing and/or analysis. In some examples, the animal monitoring devices can communicate directly with a non-network client device 115 without sending data through the network 140. The term "non-network" client device does not infer it is not also connected via the cloud or other network, but merely that there is a wireless or wired connection that can be present directly with the animal monitoring device. For example, the animal monitoring devices and the non-network client device can communicate via Bluetooth. In some embodiments, the animal monitoring devices process the load sensor data directly. In many embodiments, the animal monitoring devices utilize the load sensor data to determine if the animal monitoring device is unbalanced. In this instance, automatic or manual adjustment of one or more adjustable feet can rebalance the animal monitoring device. In this way, the animal monitoring devices can adjust their positioning to provide a solid platform for the waste elimination area.

Any of the computing devices shown in FIG. 1A (e.g., client devices 110, analysis server systems 120, and animal monitoring devices 130) can include a single computing device, multiple computing devices, a cluster of computing devices, and the like. A computing device can include one or more physical processors communicatively coupled to memory devices, input/output devices, and the like. As used herein, a processor may also be referred to as a central processing unit (CPU). The client devices can be accessed by the animal owner, a veterinarian, or any other user.

Additionally, as used herein, a processor can include one or more devices capable of executing instructions encoding arithmetic, logical, and/or I/O operations. In one illustrative example, a processor may implement a Von Neumann architectural model and may include an arithmetic logic unit (ALU), a control unit, and a plurality of registers. In many aspects, a processor may be a single core processor that is typically capable of executing one instruction at a time (or process a single pipeline of instructions) and/or a multi-core processor that may simultaneously execute multiple instructions. In some examples, a processor may be implemented as a single integrated circuit, two or more integrated circuits, and/or may be a component of a multi-chip module in which individual microprocessor dies are included in a single integrated circuit package and hence share a single socket. As discussed herein, a memory refers to a volatile or non-volatile memory device, such as RAM, ROM, EEPROM, or any other device capable of storing data. Input/output devices can include a network device (e.g., a network adapter or any other component that connects a computer to a computer network), a peripheral component interconnect (PCI) device, storage devices, disk drives, sound or video adaptors, photo/video cameras, printer devices, keyboards, displays, etc. In several aspects, a computing device provides an interface, such as an API or web service, which provides some or all of the data to other computing devices for further processing. Access to the interface can be open and/or secured using any of a variety of techniques, such as by using client authorization keys, as appropriate to the requirements of specific applications of the disclosure.

The network 140 can include a LAN (local area network), a WAN (wide area network), telephone network (e.g., Public Switched Telephone Network (PSTN)), Session Initiation Protocol (SIP) network, wireless network, point-to-point network, star network, token ring network, hub network, wireless networks (including protocols such as EDGE, 3G, 4G LTE, Wi-Fi, 5G, WiMAX, and the like), the Internet, and the like. A variety of authorization and authentication techniques, such as username/password, Open Authorization (OAuth), Kerberos, SecureID, digital certificates, and more, may be used to secure the communications. It will be appreciated that the network connections shown in the example computing system 100 are illustrative, and any means of establishing one or more communication links between the computing devices may be used. Authentication can be employed to ensure that the client devices 110, the non-network client device 115, the analysis server systems 120, and the animal monitoring device 130 are authorized to receive data and notifications to and from one another. A user can employ username and password combinations to sign in and access data and/or notifications.

Figure 1B:
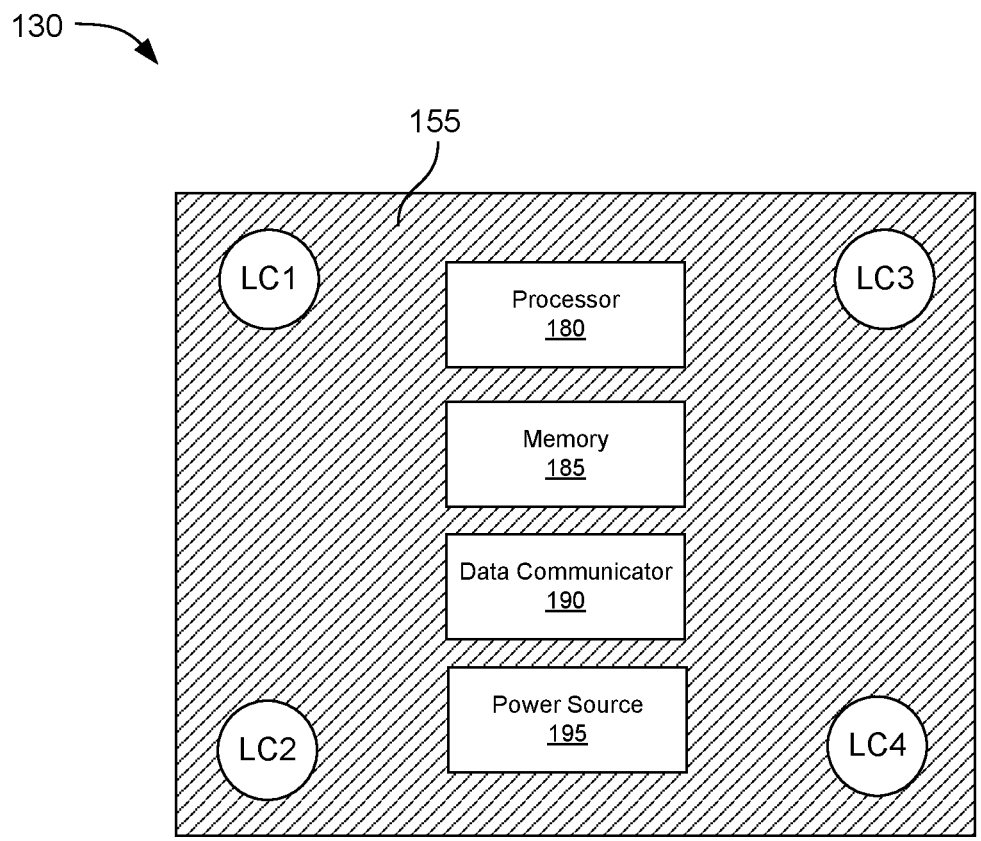
Figure 1C:
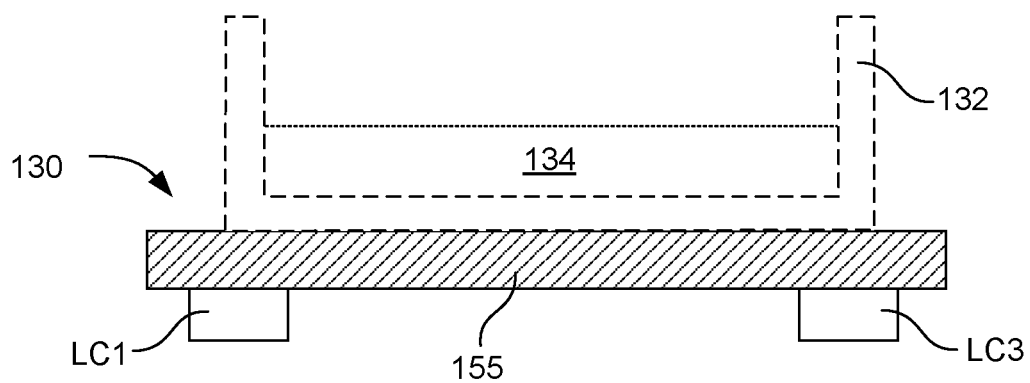
Figure 10:
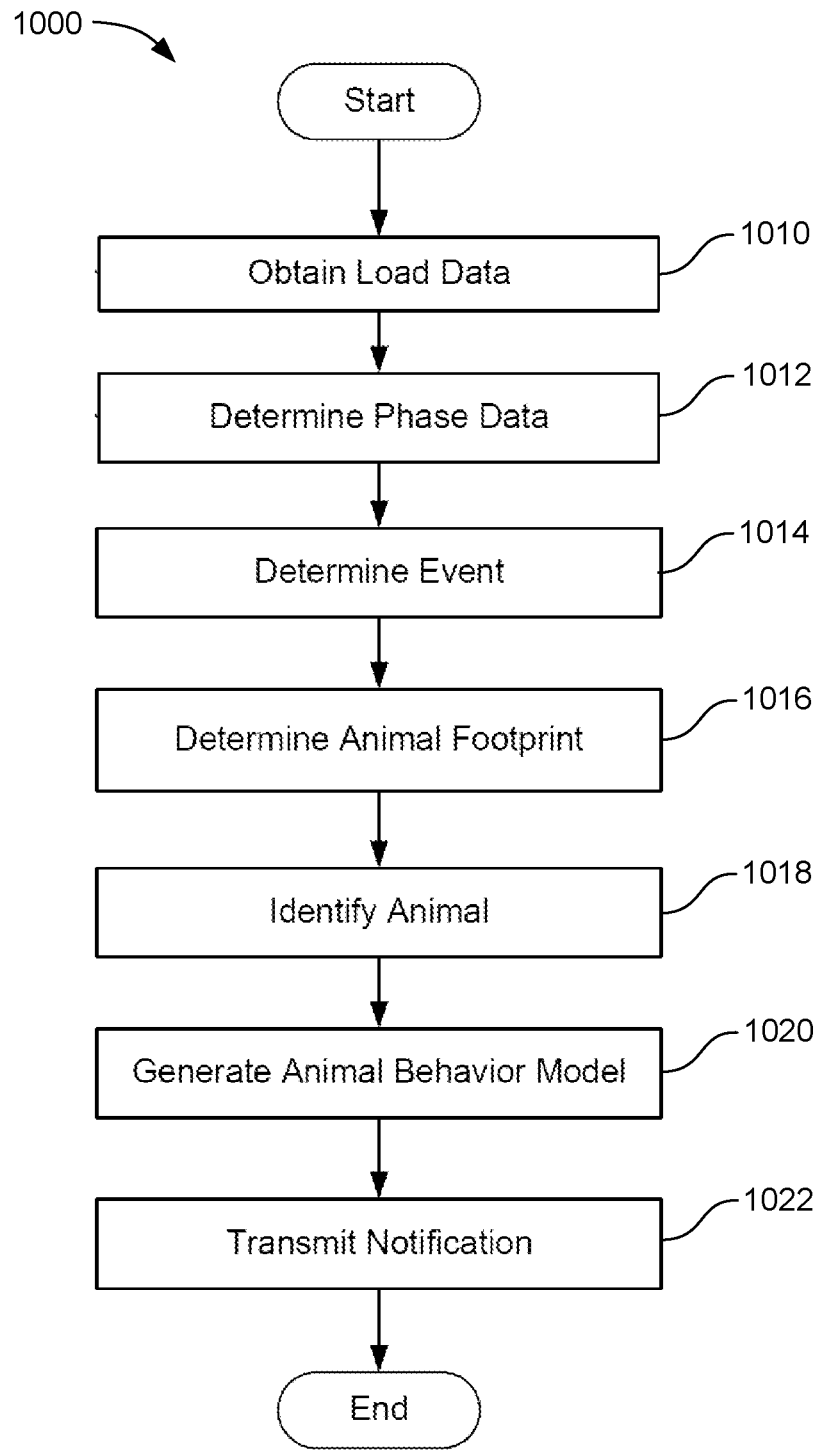
FIG. 10 illustrates a flowchart of examples of animal identification in accordance with the present disclosure.

FIG. 1B is a bottom plan view and FIG. 10 is a side plan view of an animal monitoring device 130 which can be used in the animal health monitoring systems and methods of the present disclosure. The animal monitoring device in this example includes a platform 155 that is capable of carrying or receiving contained litter above the platform. In some examples, the platform has a litter box 132 shown as it could be placed upon an upper surface of the platform. The litter box is shown containing litter 134. The litter box may be an off the shelf litter box, may be purpose built for the platform 155, or may be integrated with or coupled to the platform. The platform may be capable of carrying more than one type of litter box. The platform is depicted as rectangular in shape. However, the platform can be any shape such as a square, rectangle, circle, triangle, etc.

The animal monitoring device 130 is depicted as having four load sensors LC1, LC2, LC3, and LC4. It should be appreciated that animal monitoring devices can be capable of functioning with three or more load sensors and are not limited to four load sensors. Individual load sensors of the four load sensors are associated with the platform 155 and separated from one another and receive pressure input independent of one another. In some examples, the platform can be a triangular shape and be associated with three load sensors. The triangular shape allows animal monitoring devices to be easily placed in a corner of a room. The platform can be circular in shape and can have three or more load sensors. The platform is not limited to any type of shape and can have curved or straight lines as well as rounded or sharp corners.

The animal monitoring device 130 can include a processor 180 and a memory 185. The processor and memory can be capable of controlling the load sensors and receiving load data from the load sensors. The load data can be stored temporarily in the memory or long term. The data communicator 190 can be capable of communicating the load data to another device. For example, the data communicator can be a wireless networking device with employee wireless protocols such as Bluetooth or Wi-Fi. The data communicator can send the load data to a physically remote device capable of processing the load data such as the analysis server systems 120 of FIG. 1A. The data communicator can also transmit the data over a wired connection and can employ a data port such as a universal serial bus (USB) port including a USB-c type port. Alternatively, a memory slot can be capable of housing a removable memory card where the removable memory card can have the load data stored on it and then physically removed and transferred to another device for upload or analysis. In one embodiment, the processor 180 and memory 185 are capable of analyzing the load data without sending the load data to a physically remote device such as the analysis server systems.

The animal monitoring device 130 can include a power source 195. The power source can be a battery such as a replaceable battery or a rechargeable battery. The power source can be a wired power source that plugs into an electrical wall outlet. The power source can be a combination of a battery and a wired power source. The animal monitoring device 130 may be built without a camera or image capturing device and may not require the animal to wear an RFID collar.

Typically, a cat will enter its litter box, find a spot, eliminate, cover the elimination, and exit the litter box. An animal health monitoring system can track the activity of the cat while in the litter box using one or more load sensors that measure the distribution of the cat's weight and the overall weight of the system. This data can be processed to identify specific cat characteristics, derive features related to the cat behaviors (e.g., location of elimination, duration, movement patterns, force of entry, force of exit, volatility of event, and the like). A variety of events can be determined based on these characteristics and features. In many embodiments, a variety of machine learning classifiers can be used to determine these events as described in more detail herein. These events can include, but are not limited to, false triggers, human interactions, cat out of box interactions, and cat inside box interactions. Data analysis used for classification can use normalization logic to normalize raw data for the purposes of classification. Aggregation logic can then be employed with the normalized data to detect trends in data over time related to a unique animal. The trends can be associated with the animal's weight, average weight, weight trends, frequency patterns, time of day patterns, etc. The use of normalization techniques combined with aggregation logic can be referred to as ensemble logic. The ensemble logic can have the purpose of converting the output of data from data models to a consistent set of measurements and providing smoothed measurement trends across a variety of time periods.

In one example, the load sensors can have a sampling rate associated with gathering data while the platform is being interacted with. The sampling rate can be set to one rate or can fall within a range of sampling rates. The individual load sensors can be set to sample data at the same rate as the other sensors associated with the platform or at a different rate. In one example, the sampling rate has a range from 2.5 Hz to 110 Hz. In one example, the sampling rate has a range of 20 Hz to 110 Hz. In one example, the sampling rate is 40 Hz. It should be appreciated that the load sensors can be separate and independent of one another while being associated with the same platform. Data recorded or sampled by the load sensor independent of one another can allow for analysis of the data to determine unique features of an animal's interaction with the device. For example, a path of movement across the platform as well as entering and exiting the platform can be determined. Patterns of movement as well as weight can be used to determine the identity of an animal. A platform can have a minimum of three load sensors or can have more than three load sensors regardless of the shape of the platform. In one example, the load sensors can include a full bridge configuration with a rounded point contact. In one example, the platform has an X-axis dimensional measurement from 400 mm to 600 mm and a Y-axis dimensional measure from 250 mm to 450 mm. In one example, the individual load sensors can each have a maximum load capacity which may or may not be the same as one another. For example, the individual load sensor may each have a maximum load capacity of 10 kg. The individual load capacity of the load sensors taken as a whole can limit the amount of weight that can safely be placed on the platform and have the device work properly. The total amount of weight placed on the platform can include the weight of the litter box, the litter, and the animal in the litter box. The maximum weight capacity of the device can be less than the average weight of an adult human. Therefore, in some examples, a human standing on the platform can cause the platform to not function. The maximum weight capacity of the device can be selected based on the average weight of an animal interacting with the device such as a cat.

Figure 1D:
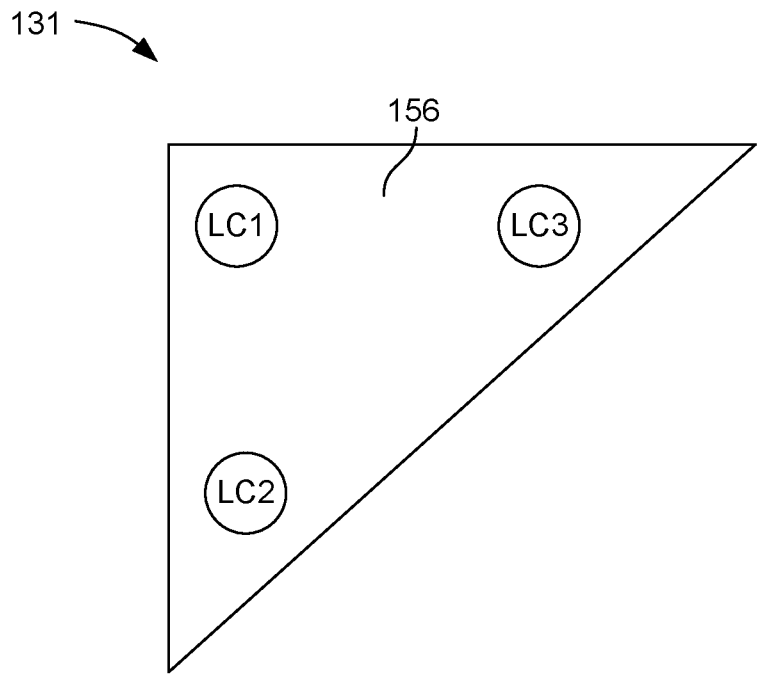

FIG. 1D depicts a bottom plan view of an animal monitoring device 131 which can be used in the animal health monitoring systems and methods of the present disclosure. The animal monitoring device can include a platform 156 that is substantially triangular in shape. The platform can have at least three load sensors or more. The animal monitoring device 131 can include some or all of the features and accessories as described and depicted for the animal monitoring device 130 such as a processor, memory, data communicator and power source. The triangular shape of the platform can be any type of triangle and can be well suited to fit into the corner of a room such as a bathroom.

Figure 1E:
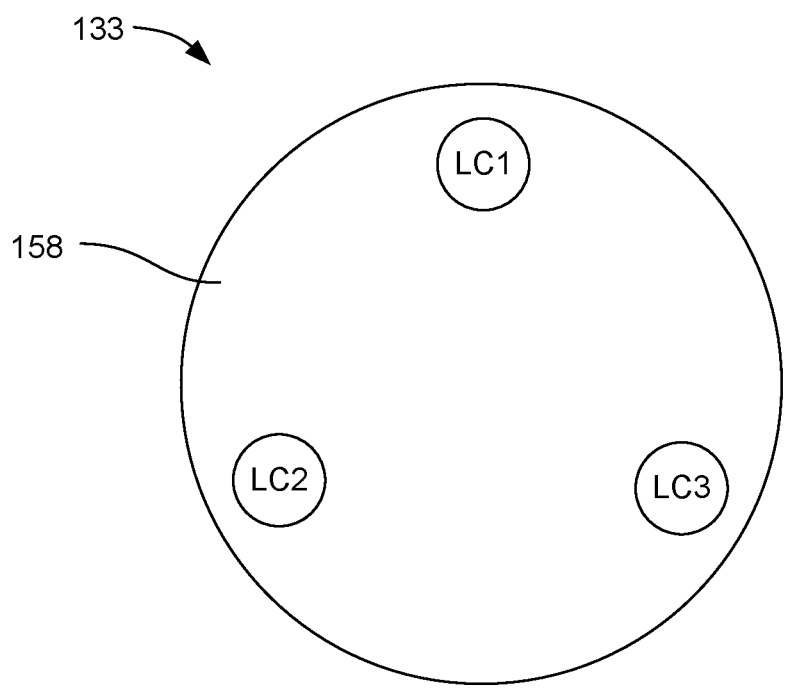

FIG. 1E depicts a bottom plan view of an animal monitoring device 133 which can be used in the animal health monitoring systems and methods of the present disclosure. The animal monitoring device can include a platform 158 that is substantially circular in shape. The platform can have at least three load sensors or more. The animal monitoring device 133 can include some or all of the features and accessories as described and depicted for the animal monitoring device 130 such as a processor, memory, data communicator and power source. The circular shape of the platform can be any size of circle or can be an irregular circular shape including an ellipse or oval.

The platform 155 can have a foam pad adhered to the surface of the platform. The foam pad can be used to interface between the platform and the container 132. The foam pad can cushion the contact between the platform and the container as well as provide resistance to the container slipping on top of the platform. The foam pad can be imprinted with designs such as a logos or other features. The imprinted designs may have functional uses such as a resistance to slipping. The platform can also have physical buttons for a user to interact with the platform such as on/off, reset, pairing, tare, and other buttons. A tare button can be used to reset the weight of the litter box and litter after changes have been made such as changing the litter or replacing the litter box itself. The platform can include other hardware features to output information to users such as a display or speakers. Buttons can be used to navigate an interface on the display and select options. The platform can have adjustable feet on the bottom of the platform used to adjust the height of the platform and to stabilize and level the platform on an uneven surface.

Figure 2:
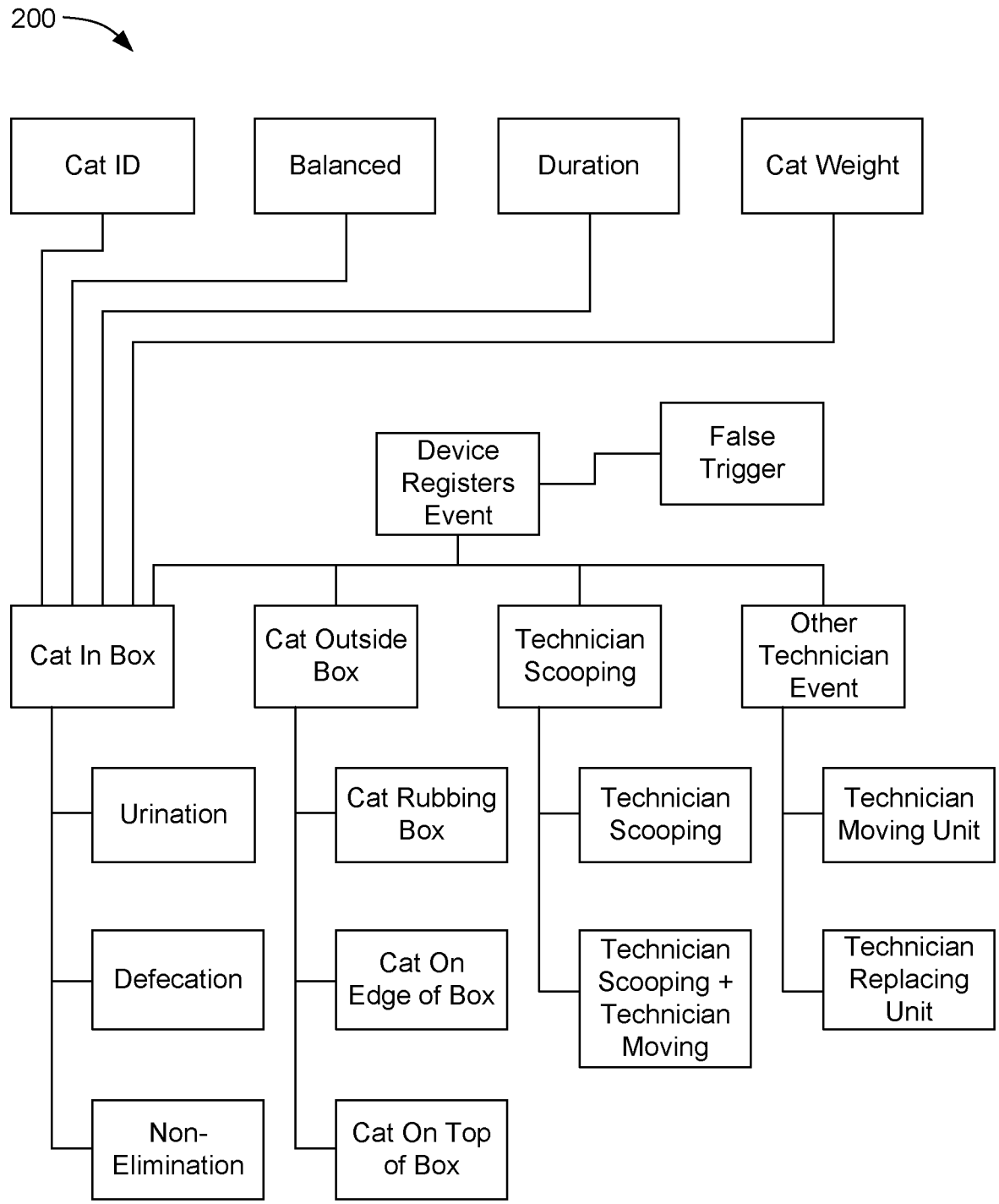
FIG. 2 illustrates a conceptual overview of example events that may occur using animal health monitoring systems in accordance with the present disclosure.

FIG. 2 illustrates a conceptual overview of events occurring within an animal health monitoring system according to an example aspect of the present disclosure. The events 200 can include false triggers, cat in box events, cat outside box events, scooping events, and other events. A false trigger can indicate that some data was obtained from the load sensors, but no corresponding event was occurring. Cat in box events can include elimination events (e.g., urination and/or defecation) and non-elimination events. When a cat in box event is detected, a variety of characteristics of the cat can be determined. These characteristics include, but are not limited to, a cat identification (cat ID), the balance of the device, a duration of the event, and a weight of the cat. Cat outside box events can include the cat rubbing the litter box, the cat standing on the edge of the litter box, and/or the cat standing on top of the litter box. Scooping events can include events where litter and/or waste are being removed from the litter box by a technician. Scooping events can include scooping the litter box, adding litter to the litter box, and moving the litter box. For example, a user may pull the litter box towards them and/or rotate the litter box to gain more ready access to all portions of the litter box for complete waste removal. Other events can include moving of the animal health monitoring system and/or litter box by a user. For example, a user can move the animal health monitoring system from one location to another, replace the litter box located on top of an animal monitoring device, remove or replace a lid on the litter box, and the like.

The activity associated with a litter box can be represented as a graph that has a variety of peaks, valleys, flat spots, and other features as shown in more detail with respect to FIGS. 3A-6B. For example, for a cat elimination event, there is typically an initial increase in weight as the cat enters the litter box, a period of motion where the cat moves within the litter box, a pause in activity while the cat performs the elimination event, a second period of motion as the cat buries the elimination, and a decrease in weight of the litter box as the cat exits the litter box. As described in more detail herein, flat spots in the activity typically correspond to actual elimination events. In some examples, the duration of particular events provides an indication of the activities occurring during the event. For example, most mammals take approximately 20 seconds to empty their bladder and non-elimination events are typically shorter than urination events, which are shorter than defecation events. Additionally, changes in weight of the litter box after an event occurs can be an indicator of the event that occurred as urination events typically result in a larger weight increase than defecation events.

The activity can include a variety of events that can be identified and labeled using machine learning classifiers as described in more detail herein. The machine learning classifiers can be described in general terms as Artificial Intelligence (AI) models. The events can include, but are not limited to, the cat entering the litter box, an amount of movement to find an elimination spot, amount of time to find an elimination spot, an amount of time preparing the elimination spot (e.g. digging in the litter or other energy spent prior to elimination), amount of time spent covering the elimination, amount of effort (e.g., energy) spent covering the elimination, duration of the flat spot, total duration of the event, weight of the elimination, motion of the animal (e.g., scooting, hip thrusts, and the like) during the elimination, step/slope detection on a single load sensor during the flat spot, the cat exiting the litter box, and motions and/or impacts involving the litter box.

Figure 3A:
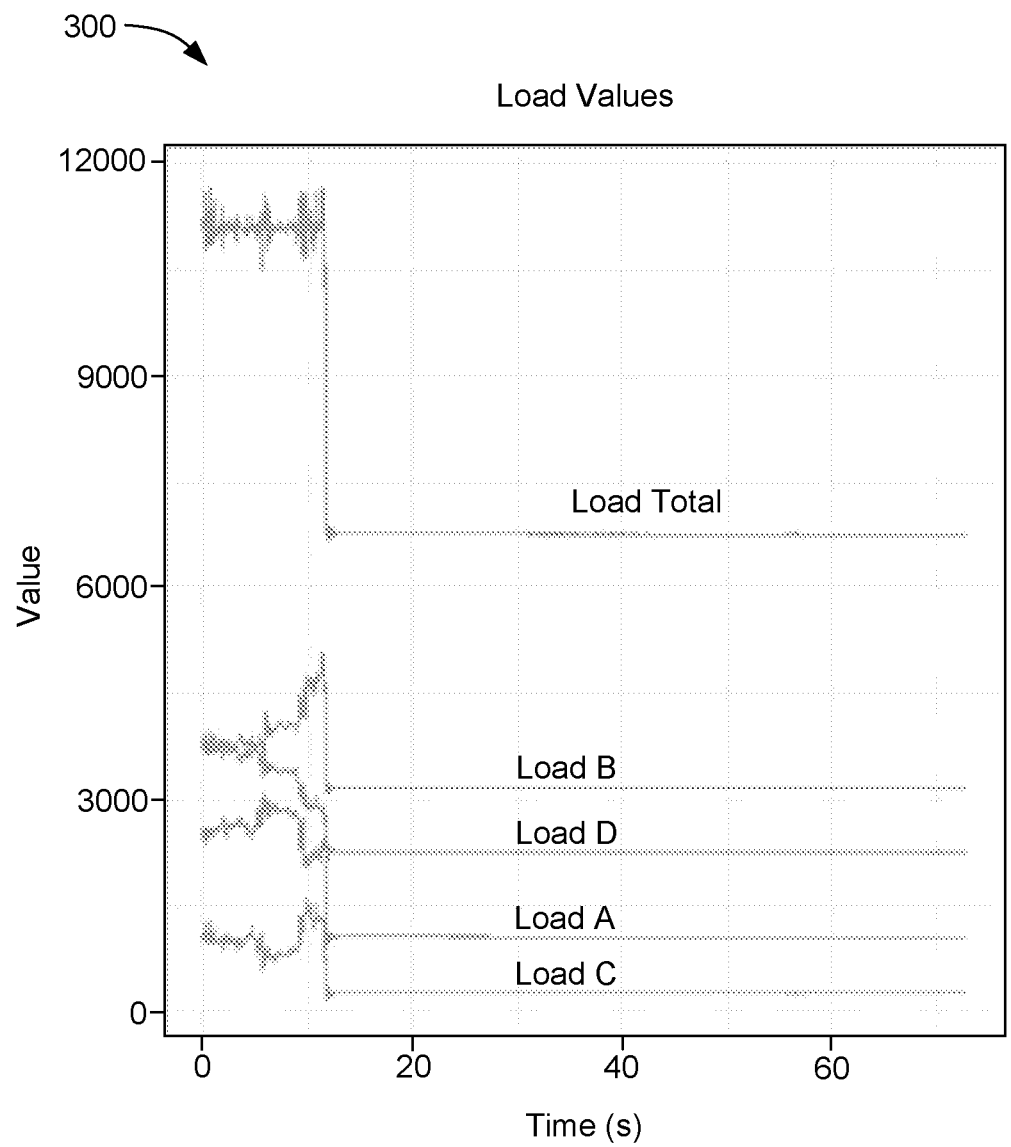
FIGS. 3A-3E illustrate example load signals for cat in box events in accordance with the present disclosure.
Figure 3B:
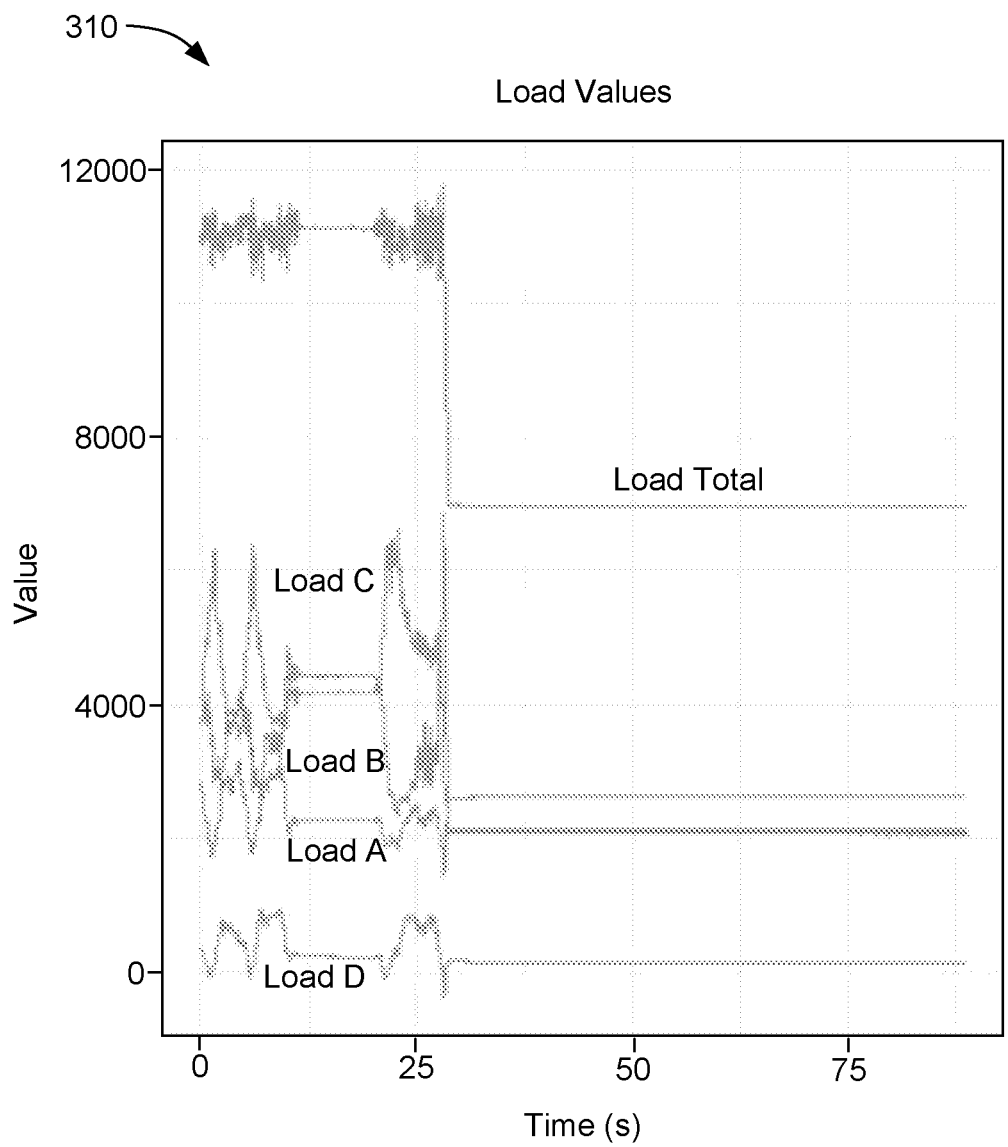
Figure 3C:
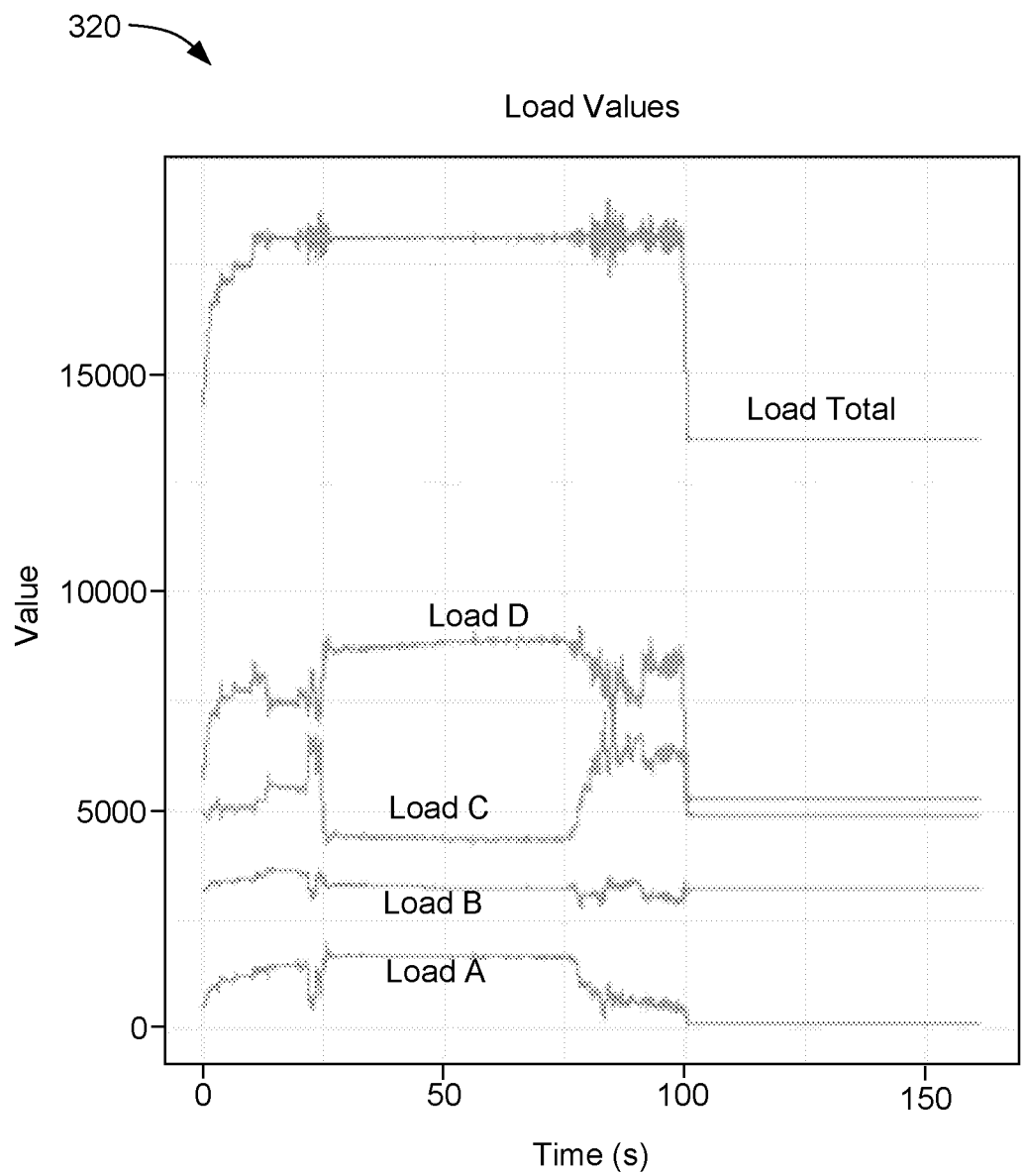
Figure 3D:
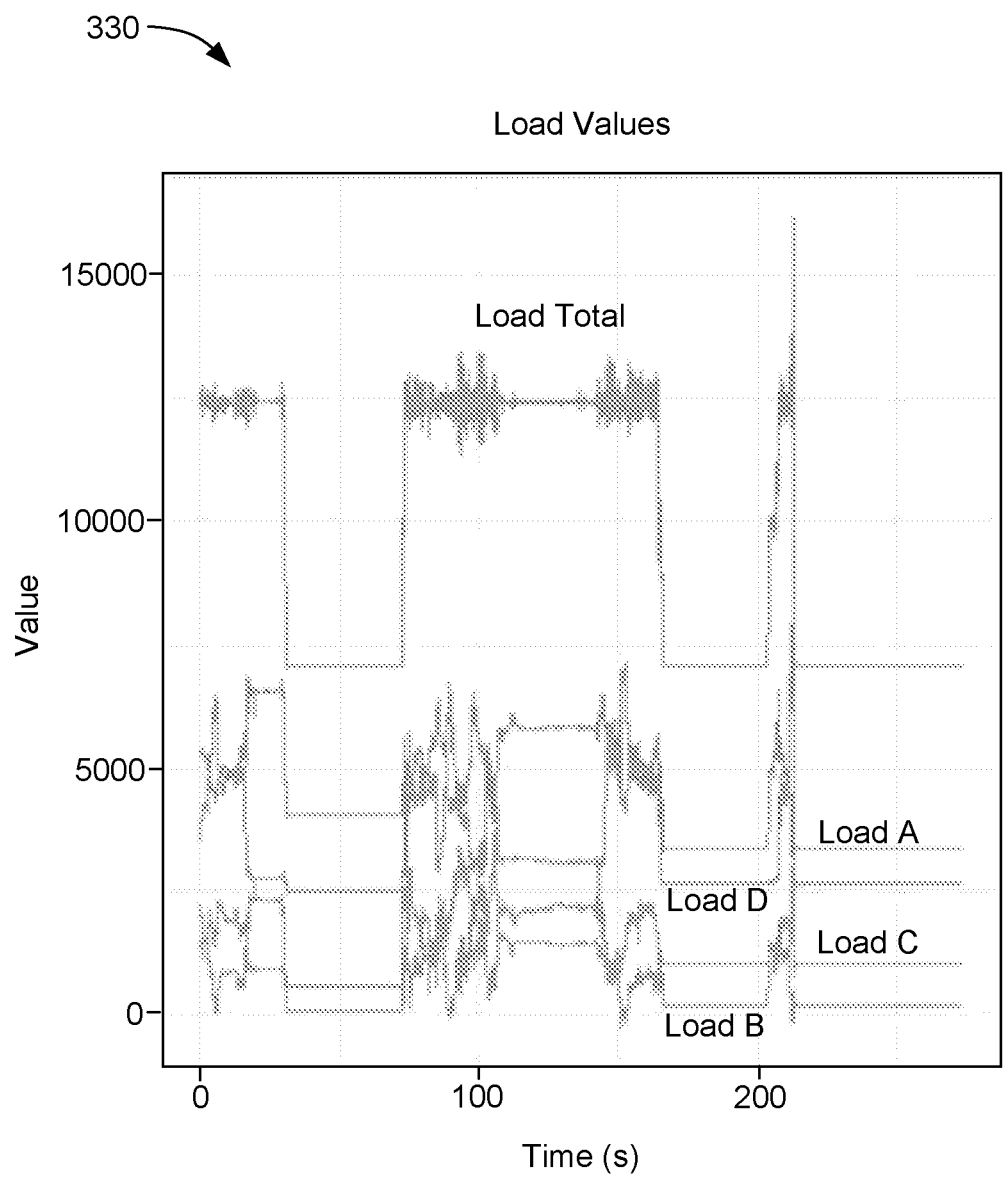
Figure 3E:
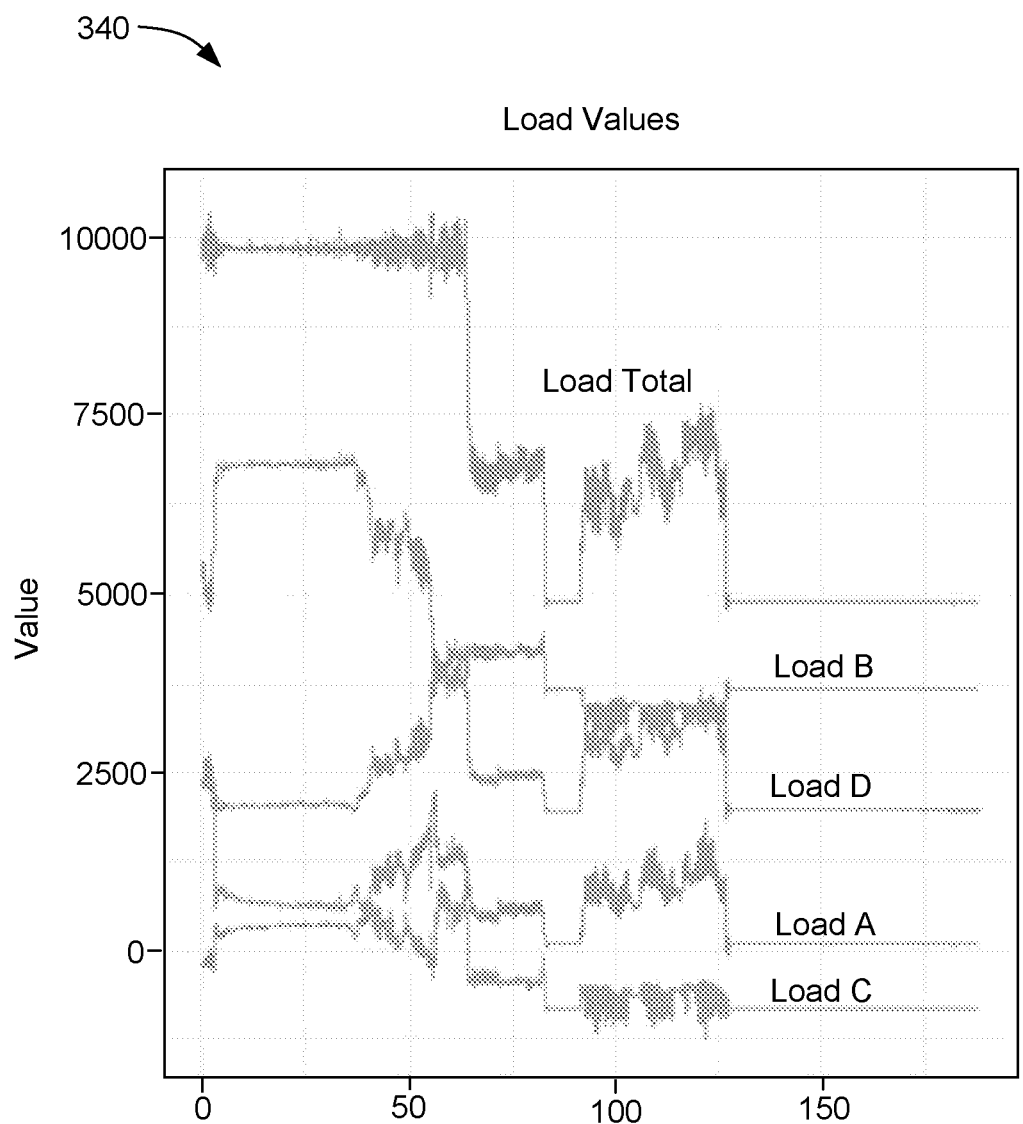

FIGS. 3A-3E illustrate load signals for cat in box events according to example aspects of the present disclosure. In FIG. 3A, a signal 300 indicating a non-elimination event is shown. In FIG. 3B, a signal 310 indicating a urination event is shown. In FIG. 3C, a signal 320 indicating a defecation event is shown. In FIG. 3D, a signal 330 indicating a non-elimination event where the cat jumps in and out of the litter box is shown. In FIG. 3E, a signal 340 indicating an event where the cat is partially located inside the litter box during a covering action is shown.

Figure 4A:
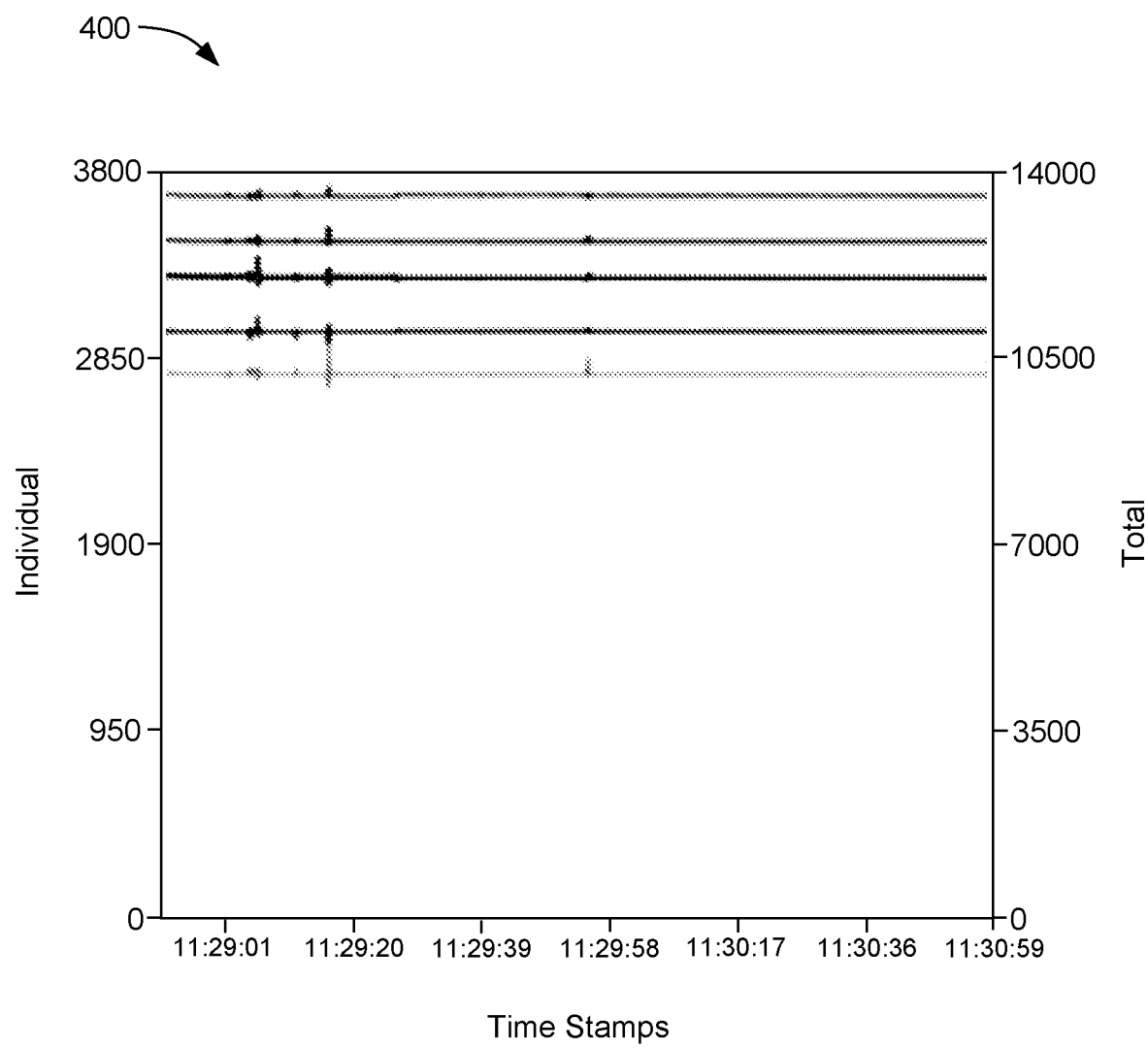
FIGS. 4A-4C illustrate example load signals for cat outside box events in accordance with the present disclosure.
Figure 4B:
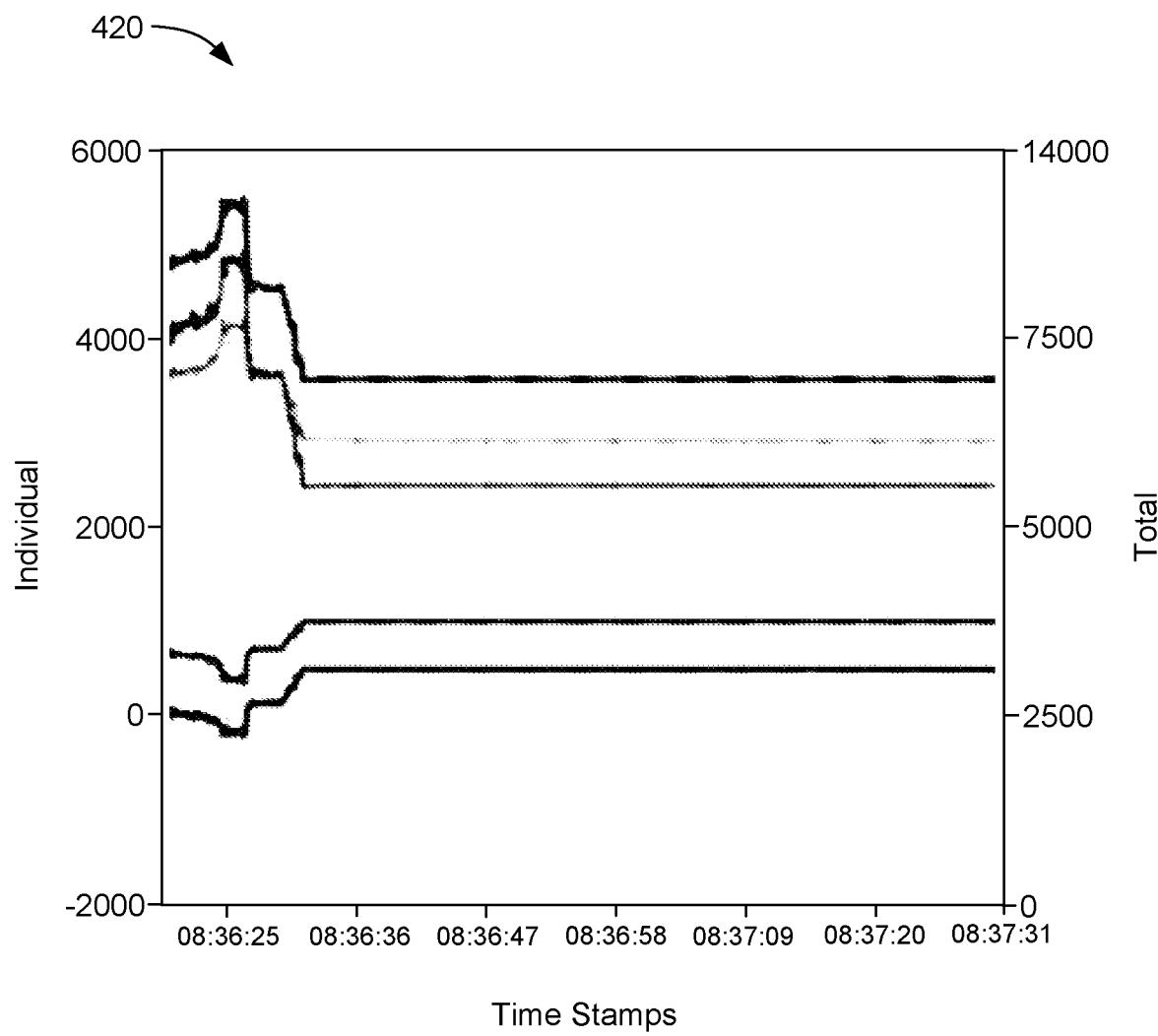
Figure 4C:
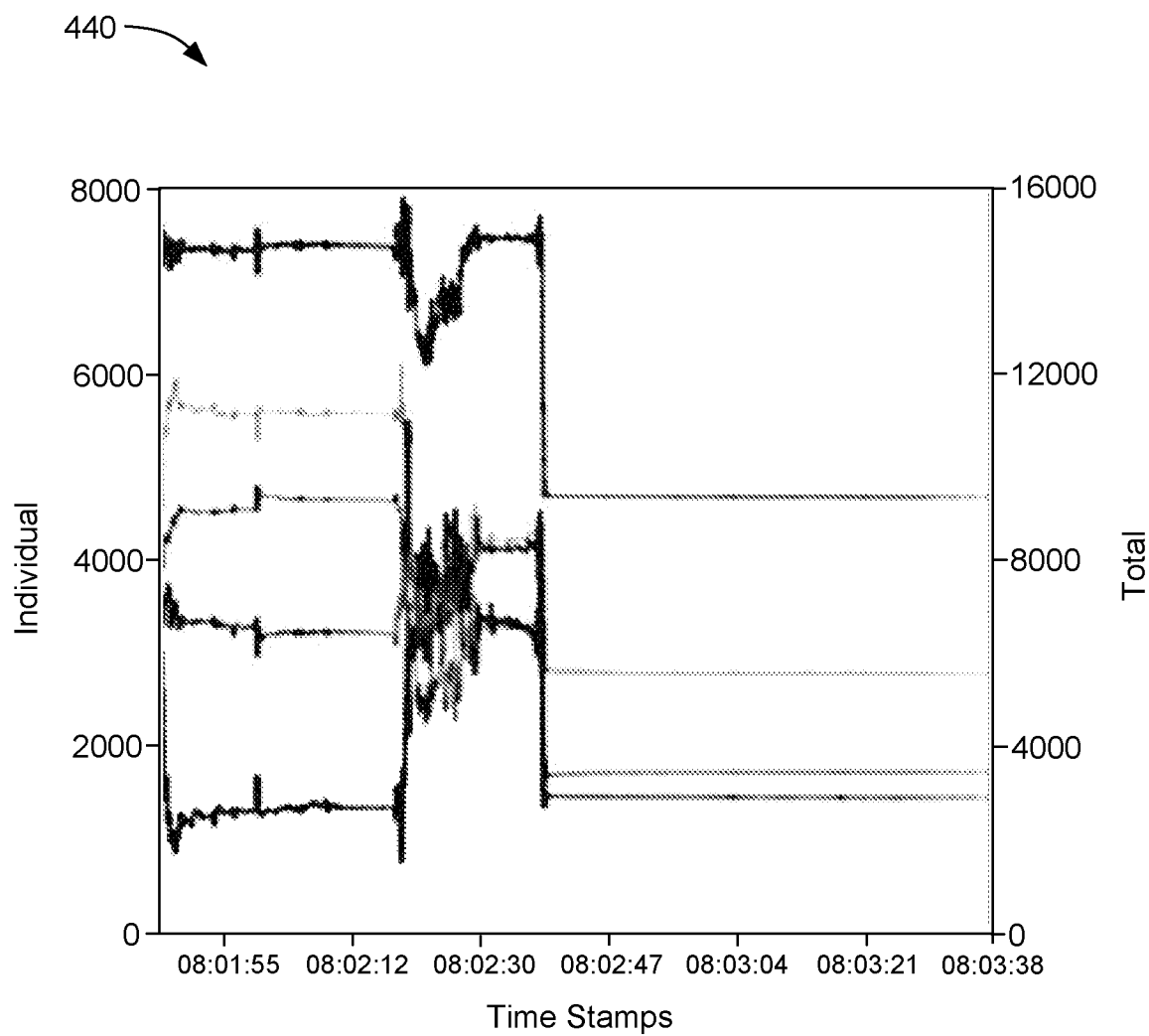

FIGS. 4A-4C illustrate load signals for cat outside box events according to example aspects of the present disclosure. In FIG. 4A, a signal 400 indicating a cat rubbing on the outside of a litter box event is shown. In FIG. 4B, a signal 420 indicating a cat standing on the edge of a litter box event is shown. In FIG. 4C, a signal 440 indicating a cat standing or sitting on top of the litter box event is shown.

Figure 5A:
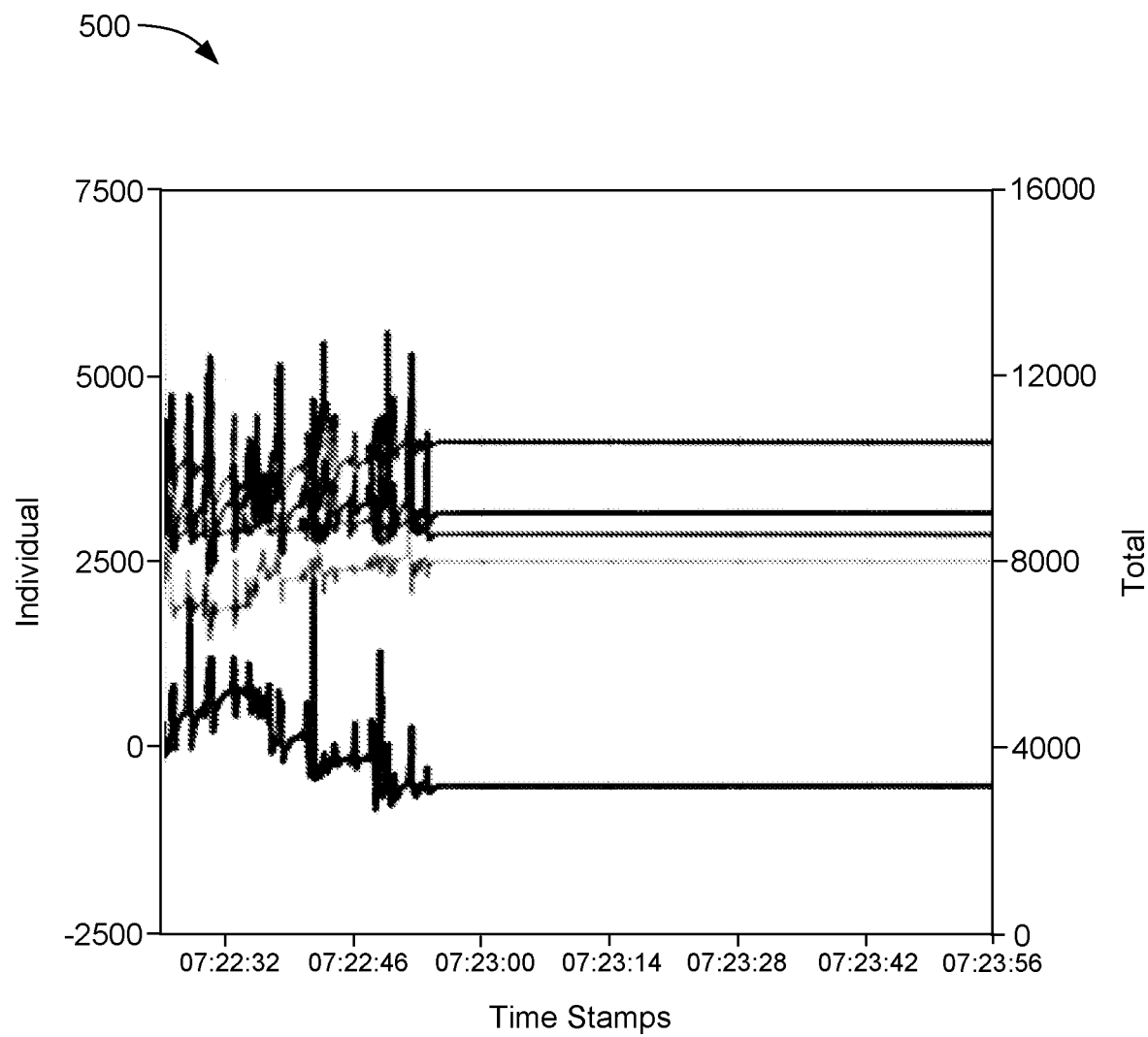
FIGS. 5A-5B illustrate example load signals for scooping events in accordance with the present disclosure.
Figure 5B:
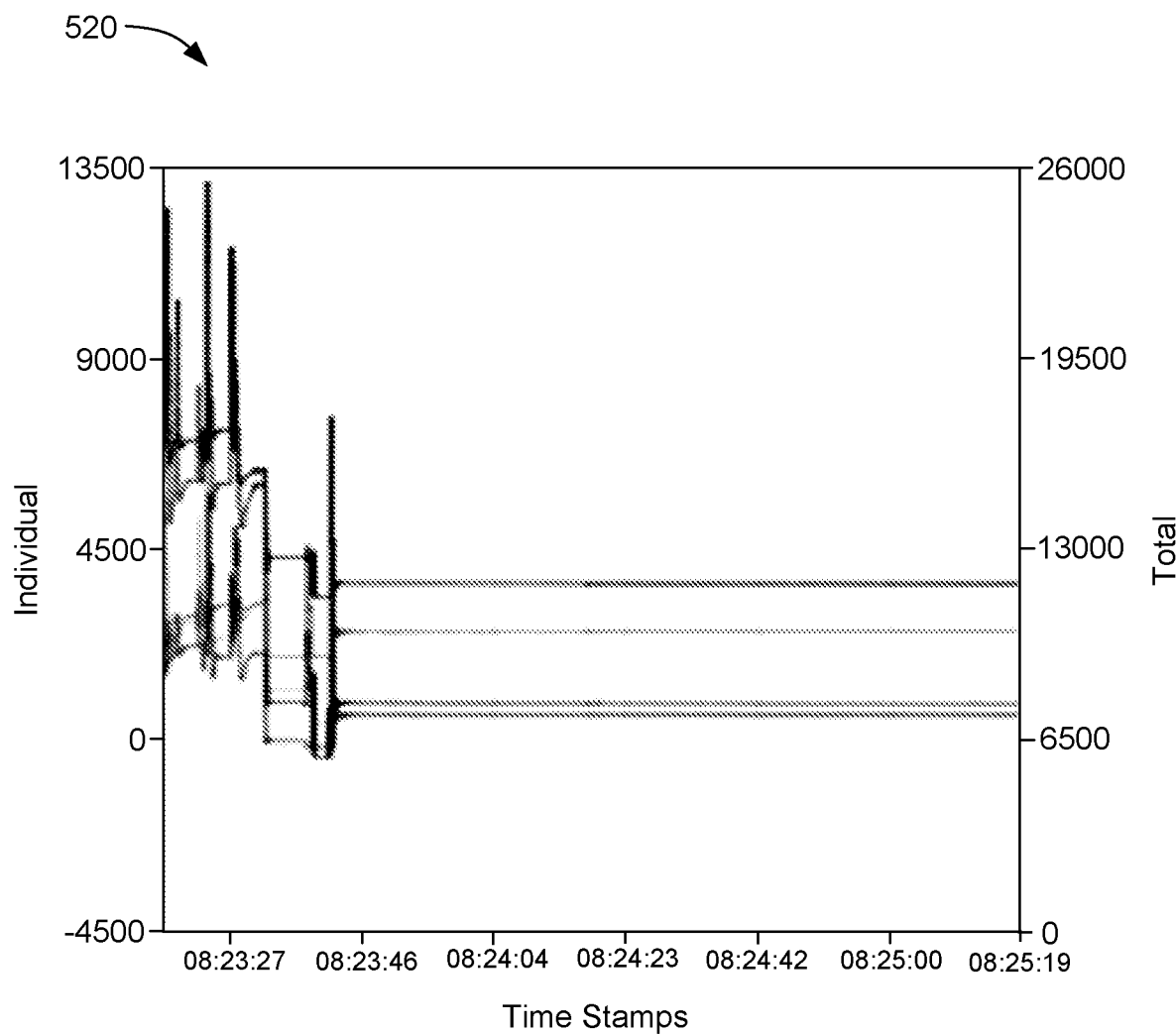

FIGS. 5A-5B illustrate load signals for scooping events according to example aspects of the present disclosure. In FIG. 5A, a signal 500 indicating a scooping event is shown. In FIG. 5B, a signal 520 indicating a scooping and moving event is shown.

Figure 6A:
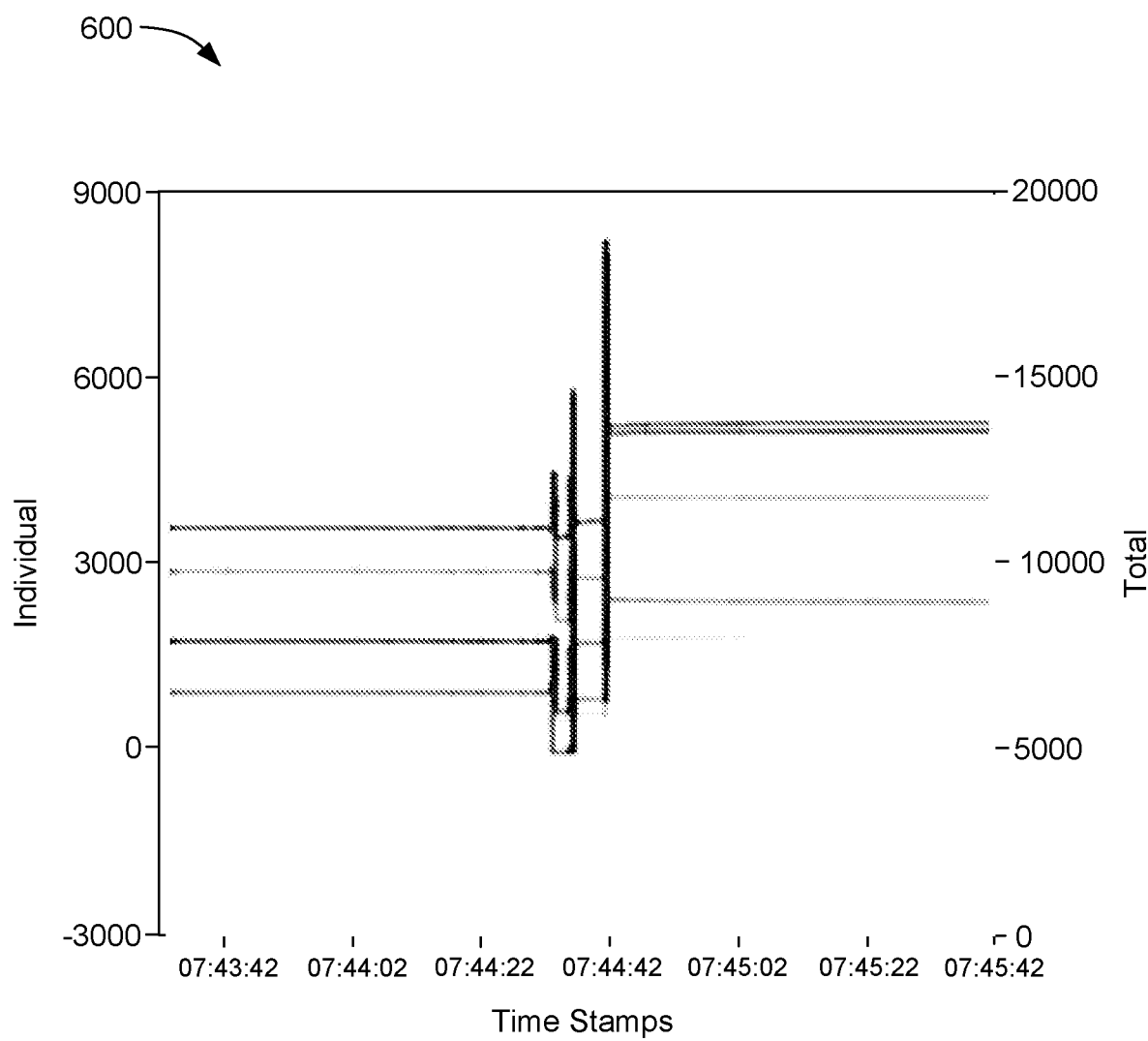
FIGS. 6A-6B illustrate example load signals for movement events in accordance with the present disclosure.
Figure 6B:
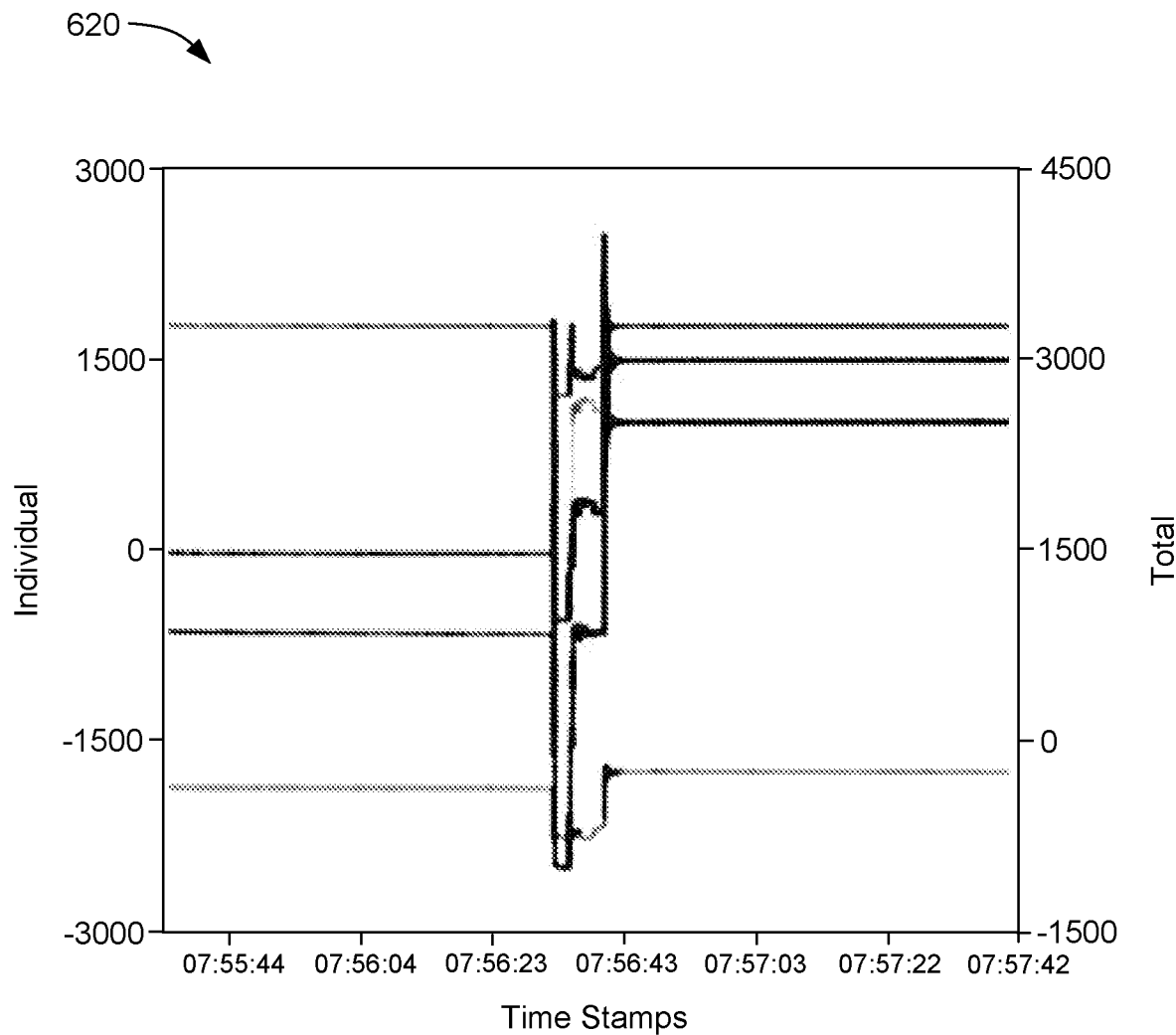

FIGS. 6A-6B illustrate load signals for movement events according to example aspects of the present disclosure. In FIG. 6A, a signal 600 indicating a litter box movement is shown. In FIG. 6B, a signal 620 indicating a measurement device movement event is shown.

An event can be conceptually divided into one or more phases for classification. For example, these phases can include a pre-elimination phase (e.g. entering, digging, finding), an elimination phase (e.g. urination, defecation), and a post-elimination phase (e.g. covering/exiting). Features can be developed in the load data for each phase to identify particular behaviors that occur during that phase. The load data can be analyzed in both the time domain and the signal domain. Time domain features include, but are not limited to, mean, median, standard deviation, range, auto-correlation, and the like. The time domain features are created as inputs for the machine learning classifier. Frequency domain features include, but are not limited to, median, energy, power spectral density, and the like. The frequency domain features are created as inputs for the machine learning classifier. For analysis associated with a single elimination event a phase separation algorithm (PSA) can separate an event into three phases for classification. For analysis associated with two eliminations (e.g. both urination and defecation) the PSA can separate an event into five phases including a first pre-elimination, a first elimination (urination), a second pre-elimination, a second elimination (defecation), and a post elimination phase.

Figure 7:
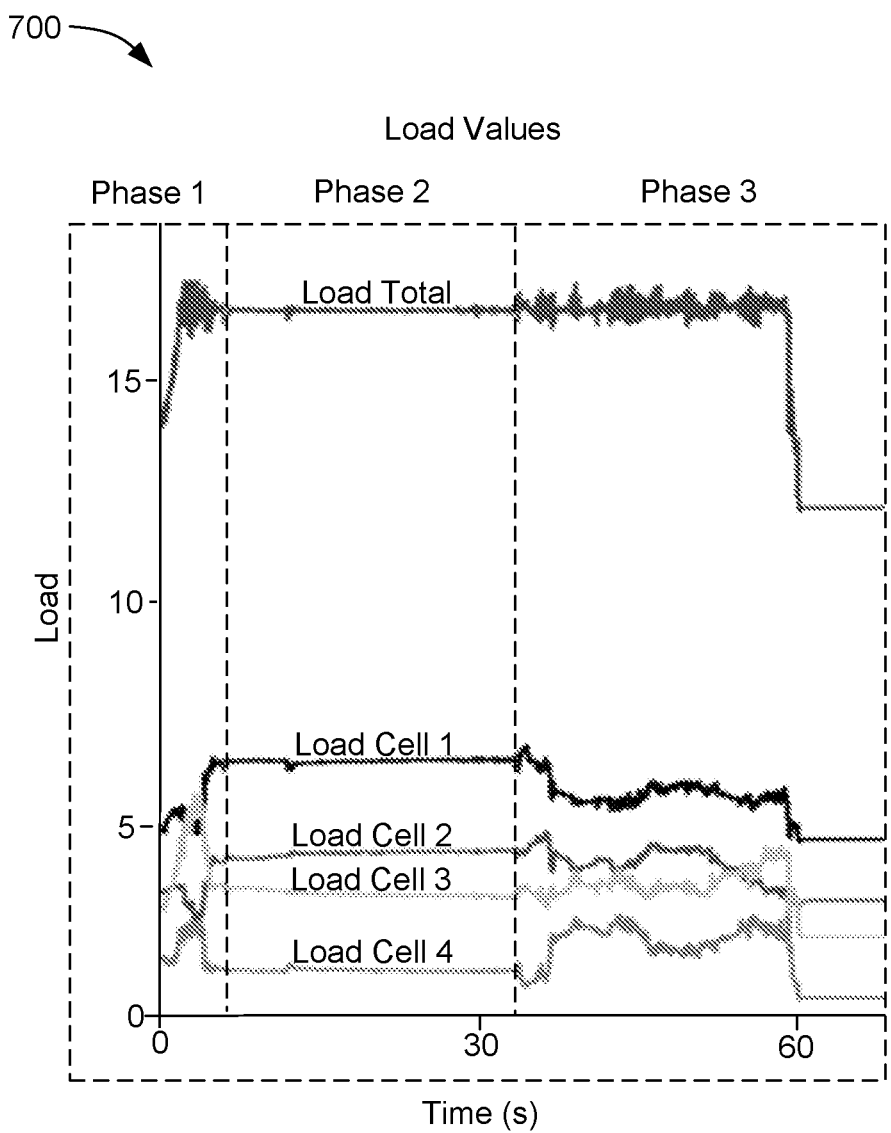
FIG. 7 illustrates example phases within an event in accordance with the present disclosure.

FIG. 7 illustrates phases within an event according to an example aspect of the present disclosure. As shown in FIG. 7, an event 700 can include three phases (e.g. Phase 1, Phase 2, and Phase 3), the measurement from each load sensor (e.g., load sensors 1-4), and a total load in the litter box. In some embodiments, the load data can be evaluated to determine the "flattest" spot in the load data, which corresponds to the elimination event (e.g., Phase 2), with data occurring prior to the flat spot being Phase 1 and data occurring after the flat spot being Phase 3. In several embodiments, consecutive sliding windows can be used to analyze the load data. Sliding windows with minimal difference (e.g., a difference below a threshold value predetermined and/or determined dynamically) in variance are grouped together as potential flat spots. The group with the largest number of samples can be selected as the flat spot for the event. In a number of embodiments, the phases are determined based on the total load value and the individual load sensor values are divided into phases along the same time steps as defined by the total load. In some embodiments, events can be determined by analyzing the total load data and/or the load data for each of the individual load sensors. In many embodiments, events can be identified by identifying potential features in the load data for each of the load sensors and aggregating the potential features to identify features within the total load data. This aggregation can be any mathematical operation including, but not limited to, sums and averages of the potential features.

In an embodiment with two eliminations and five phases, the PSA can measure and detect two of the "flattest" spots. For example, Phases 2 and 4 would be the elimination phases. Phase 2 can be a urination elimination and Phase 4 can be a defecation elimination. Phase 1 can be a pre-elimination phase associated with the animal's movement before the first elimination. Phase 3 can be a second pre-elimination phase where the animal can move within the litter box or otherwise adjust position between Phase 2 and Phase 4. Phase 5 can be a post elimination phase associated with the animal moving out of the litter box. It should be appreciated that the present technology can be employed to determine and measure multiple elimination events including more than two eliminations. The total number of phases employed by a PSA can correlate to the number of eliminations being measured with the addition of a phase before and after the first and last eliminations and a phase in between each elimination. Thus a PSA measuring a single elimination can employ three phases and a PSA measuring two eliminations can employ five phases. In one embodiment, a PSA that employs five phases may determine that an animal interaction had no eliminations, only a single elimination, or two eliminations.

In many embodiments, one or more machine learning classifiers can be used to analyze the load data to identify and/or label events within the load data. Based on the labels, the events and/or animals can be classified. It should be readily apparent to one having ordinary skill in the art that a variety of machine learning classifiers can be utilized including (but not limited to) decision trees (e.g. random forests), k-nearest neighbors, support vector machines (SVM), neural networks (NN), recurrent neural networks (RNN), convolutional neural networks (CNN), and/or probabilistic neural networks (PNN). RNNs can further include (but are not limited to) fully recurrent networks, Hopfield networks, Boltzmann machines, self-organizing maps, learning vector quantization, simple recurrent networks, echo state networks, long short-term memory networks, bi-directional RNNs, hierarchical RNNs, stochastic neural networks, and/or genetic scale RNNs. In a number of embodiments, a combination of machine learning classifiers can be utilized. More specific machine learning classifiers when available, and general machine learning classifiers at other times can further increase the accuracy of predictions.

Figure 8:
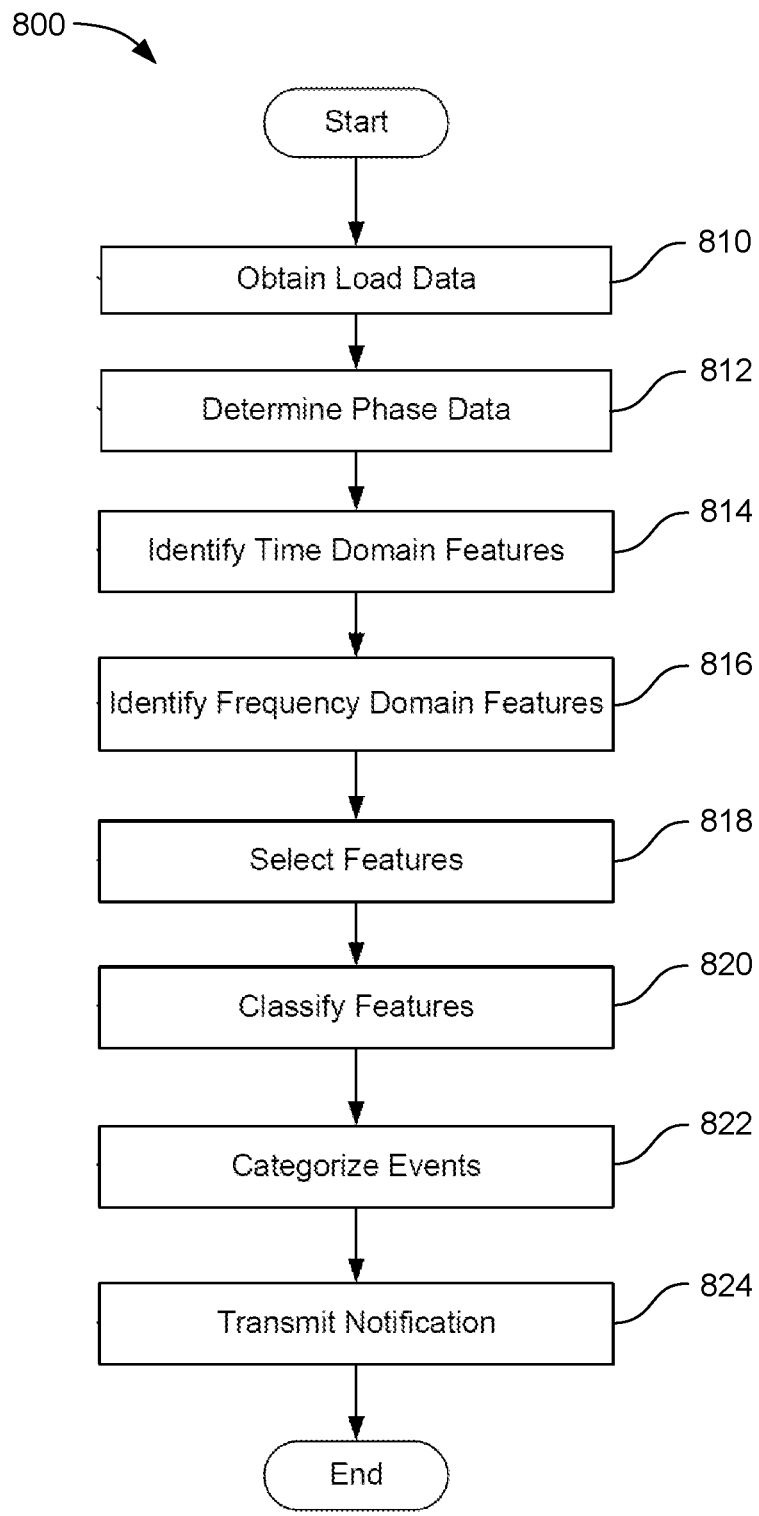
FIG. 8 illustrates an example flowchart of a method for classifying animal behavior in accordance with the present disclosure.

FIG. 8 illustrates a flowchart of a method 800 (or process) for classifying animal behavior according to an example aspect of the present disclosure. Although the method is described with reference to a flowchart, it will be appreciated that many other methods of performing the acts associated with the method may be used. For example, the order of some of the blocks may be changed, certain blocks may be combined with other blocks, one or more blocks may be repeated, and/or some of the blocks described are optional. The method may be performed by processing logic that may include hardware (circuitry, dedicated logic, etc.), software, or a combination of both. The method or process may be implemented as executed as instructions on a machine, where the instructions are included on at least one computer readable medium or one non-transitory machine-readable storage medium.

In accordance with FIG. 8, load data 810 can be obtained, such as from one or more load sensors in an animal health monitoring system as described herein. In further detail, phase data 812 can be determined, including such phase data as a finding phase, an elimination phase, and/or a covering phase as described herein. However, it is noted that this phase data is provided by example only, as different phases can be identified for different animals as appropriate. In some examples, time domain features 814 and/or frequency domain features 816 can be identified. For example, the load data can include information in the time domain, in frequency domain, or both. In some embodiments, the load data can be transformed from time domain data to frequency domain data. For example, time domain data can be transformed into frequency domain data using a variety of techniques, such as a Fourier transform. Similarly, frequency domain data can be transformed into time domain data using a variety of techniques, such as an inverse Fourier transform. In some embodiments, time domain features and/or frequency domain features can be identified based on particular peaks, valleys, and/or flat spots within the time domain data and/or frequency domain data as described herein.

In further detail with respect to FIG. 8, features 818 can be selected, such as from the phase data, the time domain features, and/or the frequency domain features for individual load sensor and/or all load sensors. In some embodiments, features 820 can be classified, such as by the use of a machine learning classifier, and in some examples, features may be classified simultaneously by the machine learning classifier. Classifying the events can include determining labels identifying the features and a confidence metric indicating the likelihood that the labels correspond to the ground truth of the events (e.g., the likelihood that the labels are correct). These labels can be determined based on the features, phase, and/or a variety of other data.

The features that are developed may be used to classify behaviors using one or more machine learning classifiers as described herein. For example, a variety of features can be developed or created in the time domain and/or the frequency domain. These features include, but are not limited to, the standard deviation of the load, a length of a flat spot, a crossover count of mean, a unique peak count, a distinct load value count, a ratio of distinct load values to event duration, a count of max load changes in individual sensors, a medium load bin percentage, a high load bin percentage, high load bin volatility, high load bin variance, automatic correlation function lag or latency, curvature, linearity, count of peaks, energy, minimum power, a power standard deviation, maximum power, largest variance shift, a maximum Kulback-Leibler divergence, a Kulback-Leibler divergence time, spectral density entropy, automatic correlation function differentials, and/or a variation of an autoregressive model. Behaviors can thus be classified based on a correlation with the classified features. For example, the selected features can be used as inputs to machine learning classifiers to classify the behaviors. The classified behaviors can include a label indicating the type of behavior and/or a confidence metric indicating the likelihood that the label is correct. The machine learning classifiers can be trained on a variety of training data indicating animal behaviors and ground truth labels with the features as inputs.

In further detail as shown in FIG. 8, events 822 can be categorized, such as may be based on the created features and/or the phase data. In some embodiments, the events can be categorized based on the confidence metric indicating the likelihood that one or more events have been correctly classified. For example, the events can be classified into elimination events, scooping events, cat sitting on litter box events, and/or any of a variety of other events as described herein. In further detail, an event can cause changes in the overall state of the animal health monitoring system. For example, adding litter, changing litter, and scooping events can cause the overall weight of the litter box to change. In these cases, the animal health monitoring system can recalibrate its tare weight to maintain the accurate performance of the animal health monitoring system.

A notification 824 can be transmitted, which may include notification related to indicating the animal's behavior generated based on the categorized event and/or historical event for the animal. In some embodiments, the notification can be generated based on events for other animals in the same cohort as the animal. The notification can indicate that an event has occurred and/or can indicate one or more inferences regarding the animal. For example, the animal's urination behavior can be tracked over time and, if there is an increase or decrease in urination activity (a decrease could be due to straining or an increase in non-elimination visits to the litter box), a notification can be generated indicating that the animal may have a urinary tract infection or other disease requiring medical attention. However, any behavior and/or characteristic of the animal (such as weight) can be used to trigger the notification generation. In some embodiments, a notification is transmitted once a threshold amount of data and/or events has been determined. The notification can be transmitted to a client device associated with the animal's owner and/or the animal's veterinarian as described herein. In a number of embodiments, the notification provides an indication requesting the user confirm that the detected event is correct. In this way, the notification can be used to obtain ground truth labels for events that can be used to train and/or retrain one or more machine learning classifiers.

As previously described, load data can be analyzed as a total load, an individual load per load sensor, and/or at a phase level via a phase separation algorithm separating the load data into phases. Example phases may include pre-elimination (e.g. entering, finding, digging), elimination (e.g. urination, defecation), and post-elimination (e.g. covering, exiting). In addition to these features, the animal's behavior and location can also be determined. In several embodiments, the animal's location within the litter box can be determined based on the location of the center of gravity of the animal within the litter box at various times during the event. By tracking the animal's center of gravity, the location of the animal within the litter box can be determined for each phase and/or each feature within the event.

Figure 9A:
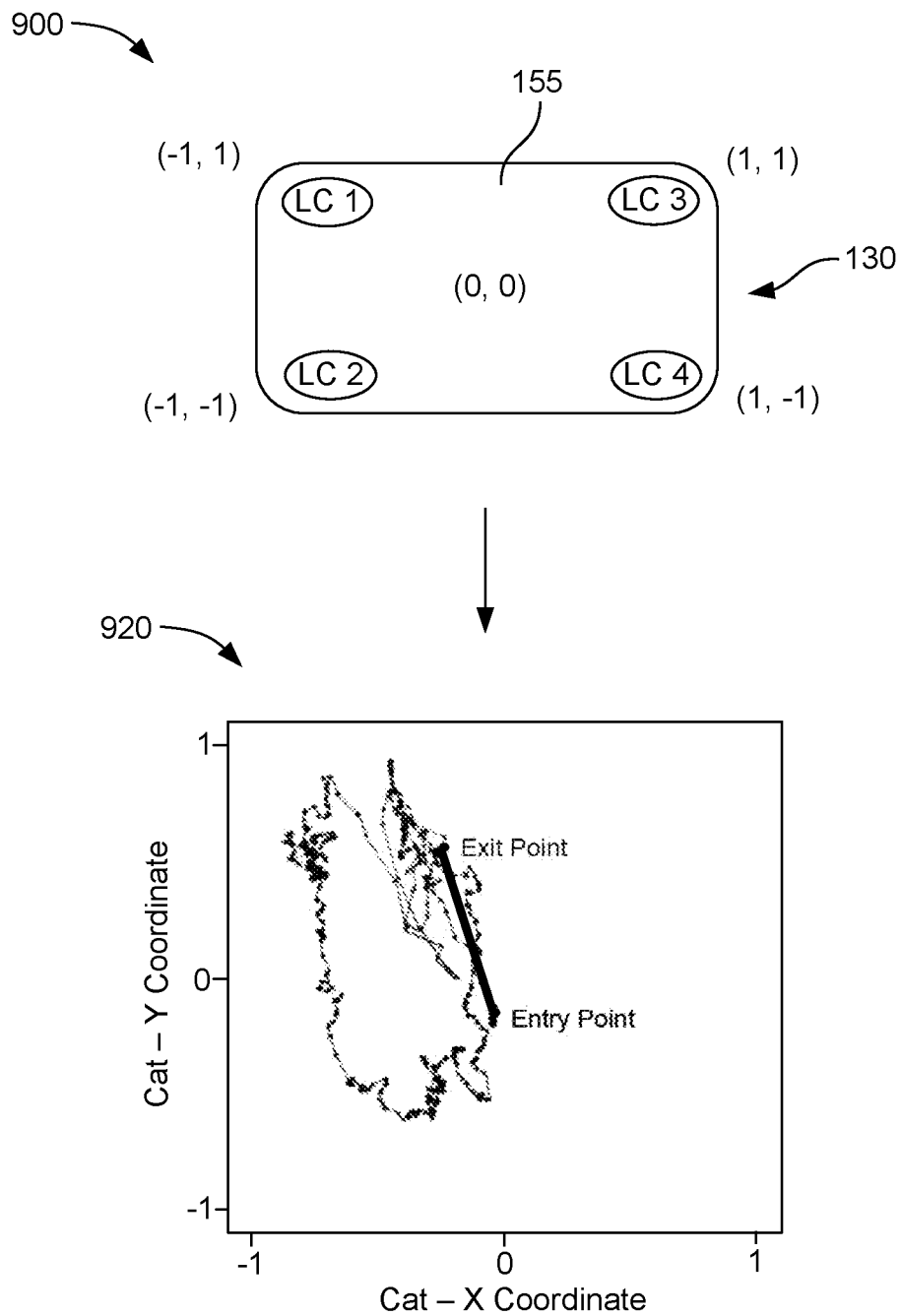
FIG. 9A illustrates example locations of an animal's movement path in accordance with the present disclosure.

FIG. 9A illustrates an example of location tracking 900 of an animal's movement path according to an example of the present disclosure. The animal's movement path within the litter box can be described from the entry to the exit of a litterbox. The movement path can be tracked using the animal's center of gravity. In this example, an animal health monitoring system may be used that includes an animal monitoring device 130 which includes a platform 155 and multiple load sensors LC1, LC2, LC3, and LC4, each located proximate to a corner of a litter box of the platform. The animal monitoring device would carry a litter box with contained litter thereon (not shown). For convenience, a coordinate system can be defined where the center of the platform (which may be aligned with the center of the litter box) is defined as (0, 0), a first corner approximately where LC1 resides is defined as (−1, 1), a second corner approximately where LC2 resides is defined as (−1, −1), a third corner approximately where LC3 resides is defined as (1, 1), and a fourth corner approximately where LC4 resides is defined as (1, −1).

In this example, the initial center of gravity of the animal health monitoring system can be calculated based on the tare (empty) weight of the animal health monitoring device with the contained litter carried thereon. When the animal enters the litter box, each load sensor can obtain a different load measurement depending on the animal's location within the litter box. At a given time, the center of gravity of the animal can be calculated based on the measurement from each of the load sensors. Graph 920 shows various locations of the center of gravity of the animal while in the litter box resting on top of the animal monitoring device, including approximate entry and exit points. As individual animals have their own unique personality, habits and routines, the general movement of the animal during a particular class of event is typically unique to that animal. In this way, the animal's movement data can be used as a signature to identify the animal during a particular event.

In addition to an animal's movement patterns for a particular event, a variety of other characteristics of the event can be used to classify events and/or identify particular animals. These characteristics include, but are not limited to, the weight of the animal, the time at which the animal typically performs a particular class of event, the location of the animal during one or more phases of the event, covering behavior (e.g., covering in place, exiting and returning to the litter box to cover, standing halfway in the litter box to cover, paw the litter box, and the like), climbing over the edge of the litter box versus jumping into the litter box, total duration of inside box activity, litter box preference for one unit over another in multi-unit environments, typical weight of elimination, times of entry/exit before eliminating, time spent digging before/after eliminating, force used to cover elimination, speed of paw movements for covering, patterns of movement within the litter box (e.g., clockwise and/or counterclockwise movement), consistency in choice of elimination spot, and order of cats entering the box in a multiple cat home.

Figure 9B:
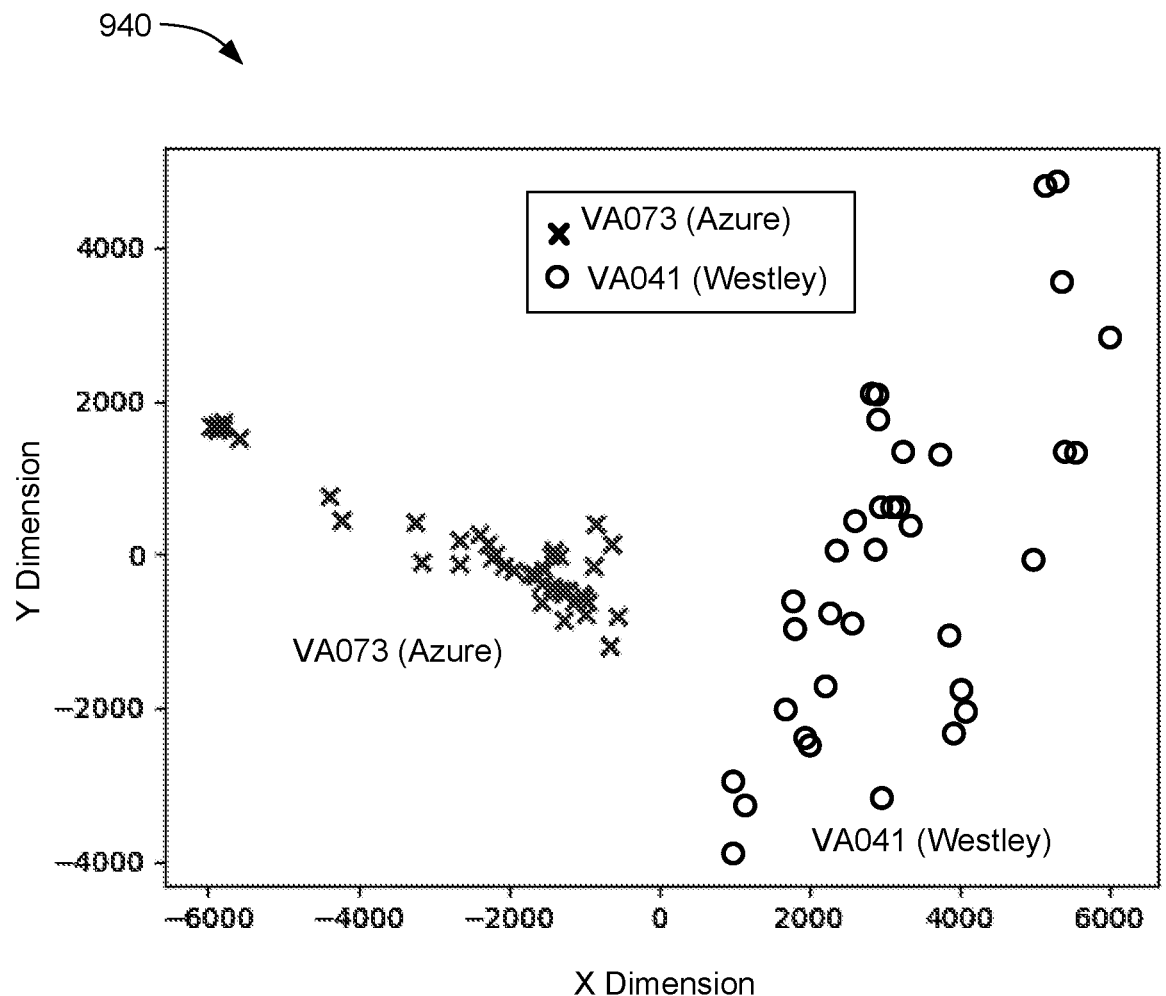
FIGS. 9B-9C illustrate examples of identifying animals based on animal behavior in accordance with the present disclosure.
Figure 9C:
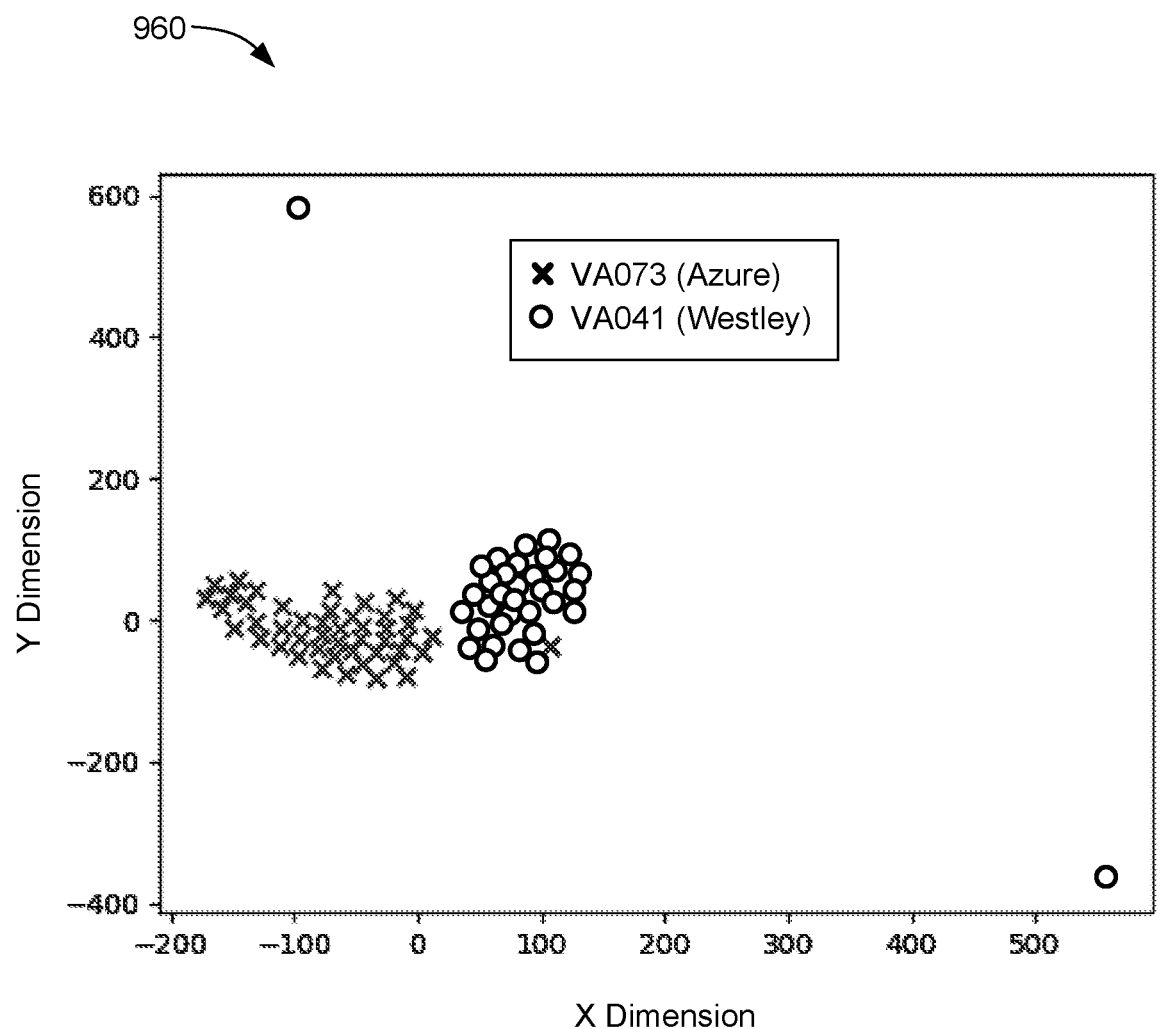

Many pet owners have multiple animals that utilize the same litter box. Thus, the animal health monitoring systems of the present disclosure can be tuned or adapted to distinguish between multiple animals using the same litter box. In accordance with this, examples are provided at FIG. 9B and FIG. 9C illustrating the identifying of animals based on animal behavior, even when there are multiple animals that use the same litter box. For example, a machine learning classifier can select a variety of features related to cat in box behavior. Furthermore, principal components analyses (PC1, PC2, etc.) can be performed as a dimension reduction technique on all features to create the top two principal components that are a combination of those features. The plots shown at 940 and 960 in FIGS. 9B-9C, respectively, show PC1 vs PC2 separated by individual cats which illustrates how features can be used to cluster cats and assign an animal identifier. Data processing used to analyze the data from the load sensors that is employed to identify an animal can employ normalization logic. Normalization logic can be used to resolve conflicts in data between different types of events. The normalization logic can take input from a user to correct the output of the data analysis. For example, a user can correct the identify of a cat.

FIG. 10 illustrates a flowchart of a method 1000 (or process) for animal identification according to an example of the present disclosure. Although the method is described with reference to the flowchart illustrated in FIG. 10, it will be appreciated that many other methods of performing the acts associated with the method may be used. For example, the order of some of the blocks may be changed, certain blocks may be combined with other blocks, one or more blocks may be repeated, and/or some of the blocks described are optional. The method may be performed by processing logic that may include hardware (circuitry, dedicated logic, etc.), software, or a combination of both. The method may be implemented as a method and executed as instructions on a machine, where the instructions are included on at least one computer readable medium or one non-transitory machine-readable storage medium.

In accordance with this method 1000, load data 1010 can be obtained, phase data 1012 can be determined at block 1012, and an event 1014 can be determined, as described herein. An animal paw print 1016 (or signal) can be determined, and can be used to identify a typical movement pattern(s) for an animal during a particular class of events. The movement pattern for the animal can be determined based on a variety of features of the movement of the animal's center of gravity during an event including, but not limited to, distance covered, speed, acceleration, direction of movement, alignment, distance from entry point of the litter box to the center of the litter box, elimination spot, resting spots, and preferred quadrant of the litter box. In some embodiments, the animal's preference for a particular quadrant can be determined based on the percentage of total observations in each quadrant and the number of load observations in each quadrant as a percentage of the total number of load samples measured. In other embodiments, the animal signature can be determined by identifying and/or computing one or more features within the movement data as inputs into one or more machine learning classifiers.

In further detail, the animal can be identified 1018, such as based on the animal signature, the determined event, and/or one or more characteristics of the event. An animal behavior model 1020 can be generated, which in some examples, can indicate the animal signature for the animal for a variety of events. For example, the animal behavior model can indicate events, frequency of the events, the animal's signature for events, the animal's preferred behaviors during events, the characteristics of the events and/or the animal, and/or any other information that may be pertinent or useable, such as that also described herein.

The method 1000 can also include the transmission of a notification 1022. The notification can be generated and/or transmitted based on a particular animal performing an event. The notification can be sent to a client device(s) and may include an indication of the animal and/or any other information as described herein. A variety of notifications and techniques for providing a notification can be implemented. For example, a notification(s) can be sent to users indicating a variety of insights into the behavior of their pets. These notifications can be sent on any schedule (e.g. daily, weekly, monthly, etc.) and/or based on particular notification thresholds being met. The notifications can include summaries of any animal monitoring devices in the same household, animal preference for the different elimination locations for either urination or defecation, time of day reports indicating the animal's typical routines, indications on the best times for litter box maintenance based on the animal's activity, and/or any other insights as appropriate.

Notification thresholds can be based on any aspect of an animal that may require additional analysis, such as the animal losing or gaining more than a threshold amount of weight over a particular time frame, an increase or decrease in elimination events, more frequent or less frequent visits to the elimination area, a change in elimination routines, and/or any other factors or combination of factors indicating a potential health issue as described herein. As described in more detail below, a variety of characteristics of the animals can be provided. These characteristics can include, but are not limited to, age, sex, reproductive status, and/or body condition. These factors can be utilized to establish the notification thresholds and/or be used to provide insights when an animal reaches a certain threshold for changes in weight, visit, and/or elimination frequency. For example, the threshold of a young cat of ideal body condition would be different from that for an underweight geriatric cat.

The notifications can provide indications of potential concerns with cat health and/or emotional state. For example, fluctuations in weight and visit frequency can be early indicators for a number of disease states such as feline lower urinary tract, bladder stones, bladder crystals, renal disease, diabetes, hyperthyroidism, feline idiopathic cystitis, digestive issues (IBD/IBS), and arthritis and/or emotional wellbeing such as stress, anxiety, and cognitive decline/dysfunction. For many animals, changes in health or behavioral state can go unnoticed until symptoms become extreme. The notifications provided by animal health monitoring systems can provide early indicators of changes in an animal's health or behavior. Animal health monitoring systems as described herein can help identify these potential issues in the early stages. For example, some issues or conditions may be defined by stages, e.g., Stages I-IV. In this example, notifications may be sent to a pet owner during earlier stages, e.g., Stage I or Stage II, so that treatment can be administered before the animal's overall health is more severely affected, such as in Stage III or Stage IV.

As mentioned, in some examples, animal health monitoring systems can be used in environments having multiple animals. These animals may have distinct weights and/or the animals may be similar in weight (e.g., the weight of the animals may overlap). Existing systems that use the weight of the animal to identify the animal typically perform poorly in these systems as weight is not a unique indicator of a particular animal. In contrast, animal health monitoring systems as described herein can use a variety of models, such as feature-based models, activity models, and combinations of models to uniquely identify animals utilizing the animal health monitoring system.

FIG. 11 illustrates the performance of various classifiers or classification models according to example aspects of the present disclosure. As shown in the table at 1100, a hybrid model analyzing both the features of an event and the location of the animal during the event may equal or even outperform a single model for all numbers of cats and all classes of overlapping weights. However, it should be noted that one or more models can be used to identify animals and events in accordance with the specific applications of embodiments provided by the present disclosure.

It will be appreciated that all of the disclosed methods and procedures described herein can be implemented using one or more computer programs, components, and/or program modules. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware and/or may be implemented in whole or in part in hardware components such as ASICs, FPGAs, DSPs, or any other similar devices. The instructions may be configured to be executed by one or more processors which, when executing the series of computer instructions, perform or facilitate the performance of all or part of the disclosed methods and procedures. As will be appreciated by one of skill in the art, the functionality of the program modules may be combined or distributed as desired in various aspects of the disclosure.

Figure 12:
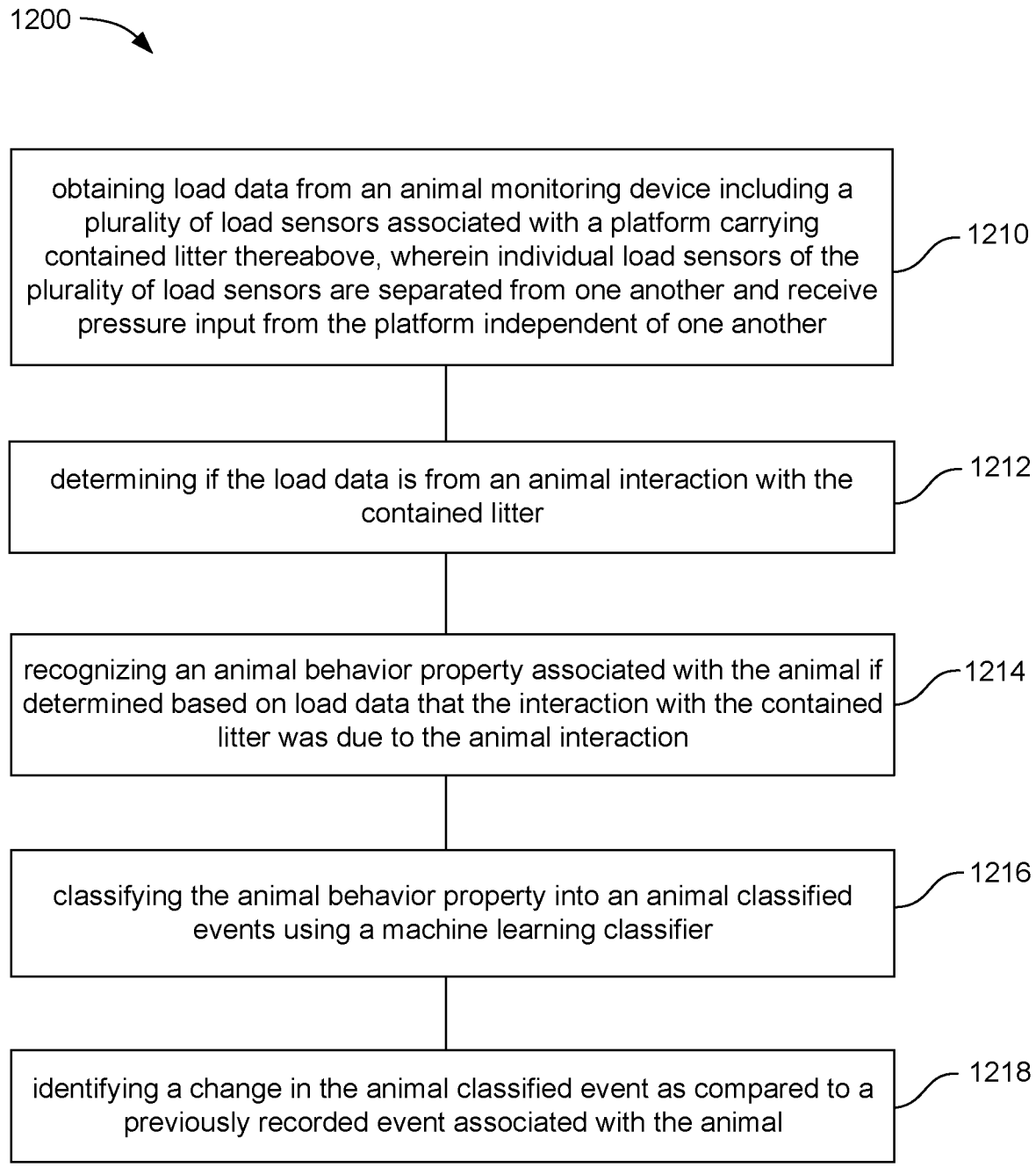
Figure 13:
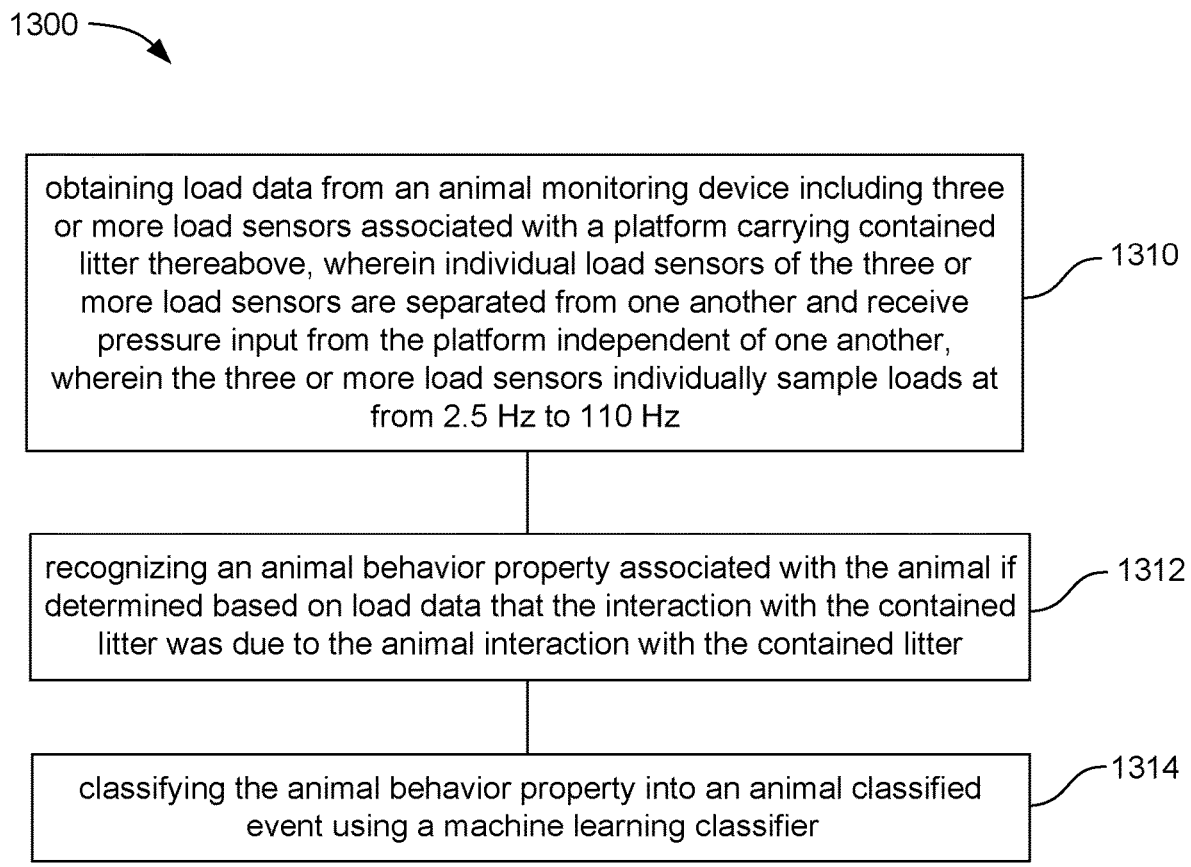

FIGS. 12-14 illustrate flowcharts of methods 1200, 1300, and 1400 (or processes) of monitoring the health of an animal according to example aspects of the present disclosure. Although the methods are described with reference to the flowcharts illustrated in FIGS. 12-14, it will be appreciated that many other methods of performing the acts associated with the method may be used. For example, the order of some of the blocks may be changed, certain blocks may be combined with other blocks, one or more blocks may be repeated, and some of the blocks described are optional. The method may be performed by processing logic that may include hardware (circuitry, dedicated logic, etc.), software, or a combination of both. The method may be implemented as a method and executed as instructions on a machine, where the instructions are included on at least one computer readable medium or one non-transitory machine-readable storage medium.

Thus, in accordance with FIG. 12, a method 1200 of monitoring the health of an animal, under the control of at least one processor, can include obtaining 1210 load data from a plurality of load sensors associated with a platform carrying contained litter thereabove. Individual load sensors of the plurality of load sensors can be separated from one another and receive pressure input independent of one another. In further detail, the method can include determining 1212 if the load data is from an animal interaction with the contained litter, recognizing 1214 an animal behavior property associated with the animal if it is determined based on load data that the interaction with the contained litter was due to the animal interaction, classifying 1216 the animal behavior property into an animal classified event using a machine learning classifier, and identifying 1218 a change in the animal classified event as compared to a previously recorded event associated with the animal.

In some examples, classifying of the animal behavior can include one or more of an in-box event, a urination event, a defecation event, or a non-elimination event. The method 1200 can further include correlating the change in the animal classified event with a physical, behavioral or mental health issue associated with the animal. In other examples, the physical health issue can be an animal disease. In other examples, the animal disease can be a feline disease selected from urinary disease, renal disease, diabetes, hyperthyroidism, idiopathic cystitis, digestive issues, and arthritis. In some examples, the mental health issue can be selected from anxiety, stress, and cognitive decline. In other examples, the behavioral issue can be outside of box elimination. In other examples, determining if the load data is from the animal interaction further determines if the load data is from the animal interaction, a human interaction, a false trigger, or an accidental interaction.

The method 1200 can further include identifying the animal based on the load data. In some examples, identifying the animal distinguishes the animal from at least one other animal that interacts with the platform. The method can likewise include generating a notification indicating the change in the animal classified event. In other examples, the notification is generated after a parameter associated with the device event meets a threshold. In other examples, the method may not include or communicate with any camera or image capturing device and does not perform visual image recognition. In some examples, classifying the animal behavior property further includes analyzing the load data from the plurality of load sensors to measure one or more of (i) a weight of a litter box positioned on the platform, (ii) a distribution of weight of the animal, (iii) a location of an event, (iv) a duration of an event, (v) a movement pattern, (vi) a force of entry, (vii) a force of exit, or (viii) a volatility of the animal interaction. In other examples, classifying the animal behavior property further includes analyzing the load data from the plurality of load sensors to identify or measure one or more of (i) the animal entering a litterbox on the platform, (ii) an amount of movement by the animal to select a particular elimination location, (iii) an amount of time to select a particular elimination location, (iv) an amount of time spent preparing (e.g. digging) the elimination location prior to elimination, (v) an amount of time spent covering the elimination, (vi) an amount of energy spent covering the elimination, (vii) a duration of the elimination, (viii) a total duration of the device event from entry to exit by the animal, (ix) a weight of the elimination, (x) a motion of the animal during the elimination, (xi) a step/slope detection on a single load sensor during the elimination, (xii) the animal exiting the litter box positioned, or (xiii) one or more motions or impacts involving the litter box.

In some examples, classifying the animal behavior property further includes analyzing load data from the plurality of load sensors in both a time domain and a frequency domain. In other examples, one or more time domain features include a mean, median, standard deviation, range, or autocorrelation created as inputs for the machine learning classifier. In other examples, one or more frequency domain features include a median, energy, or power spectral density created as inputs for the machine learning classifier. In some examples, selected features are selected from the time domain and the frequency domain, and the selected features are one or more of (i) a standard deviation of the load, (ii) a length of a flat spot, (iii) a crossover count of mean, (iv)

a unique peak count, (v) a distinct load value count, (vi) a ratio of distinct load values to event duration, (vii) a count of max load changes in individual sensors, (viii) a medium load bin percentage, (ix) a high load bin percentage, (x) a high load bin volatility, (xi) a high load bin variance, (xii) automatic correlation function lag or latency, (xiii) curvature, (xiv) linearity, (xv) count of peaks, (xvi) energy, (xvii) minimum power, (xviii) a power standard deviation, (xix) a maximum power, (xx) a largest variance shift, (xxi) a maximum Kulback-Leibler divergence, (xxii) a Kulback-Leibler divergence time, (xxiii) a spectral density entropy, (xxiv) autocorrelation function differentials, or (xxv) a variation of an autoregressive model; and wherein the animal interaction is classified and/or an animal identification is determined based on the use of the selected features as input to the machine learning classifier.

In some examples, classifying the animal behavior property in this and other methods 1200 further includes analyzing the load data from the plurality of load sensors at (i) a total load, (ii) an individual load per load sensor, and (iii) a phase level via a phase separation algorithm separating the load data into phases. In other examples, the phase separation algorithm separating the load data into phases includes at least three phases comprising pre-elimination, elimination, and post-elimination. In other examples, the method further includes determining a location of the animal within a litter box positioned on the platform. In some examples, the location of the animal within the litter box is based on a location of a center of gravity of the animal within the litter box at various times during the animal interaction. In other examples, the method further includes tracking the center of gravity of the animal to thereby determine the location of the animal within the litter box for each phase and/or each feature within the animal interaction.

In some examples, classifying the animal behavior property further includes analyzing the load data from the plurality of load sensors to determine a movement pattern for the animal, the movement pattern comprising one or more of (i) distance covered, (ii) speed, (iii) acceleration, (iv) direction of movement, (v) alignment, (vi) distance from an entry point into a litter box positioned on the platform to the center of the litter box, (vii) elimination location, (viii) resting location, or (ix) preferred quadrant of the litter box. In other examples, the preferred quadrant is determined based on a percentage of total observations in each quadrant and a number of load observations in each quadrant as a percentage of a total number of load samples. In other examples, the method 1200 further includes generating an animal behavior model for a particular animal, including identifying one or more of (i) device events by the particular animal, (ii) frequency of the device events, (iii) signature for the particular animal during the device events, (iv) preferred behaviors by the particular animal during the device events, or (v) characteristics of the device events and/or the particular animal.

A variety of user interfaces can be provided to ensure the proper installation, configuration, and usage of animal health monitoring systems. These user interfaces can provide instruction to users, solicit information from users, and/or provide insights into the behaviors and potential concerns with one or more animals.

When setting up an animal health monitoring system, the initialization and location of the animal monitoring device is important to ensuring the accuracy of the collected load data. In some embodiments, animal monitoring devices function best in an indoor, climate-controlled environment without direct sunlight. In several embodiments, animal monitoring devices should be placed at least one inch away from all walls or other obstacles as failure to provide adequate space may cause the animal monitoring devices to become stuck on obstacles, interfering with data or readings. Additionally, animal monitoring devices should be located an adequate distance from high vibration items (such as washers and dryers) or high traffic areas as the vibrations can cause false readings and/or inaccurate readings in weight sensors. In a number of embodiments, animal monitoring devices function best on a smooth, level, hard surface as soft or uneven surfaces can affect the accuracy of the load sensors. In one embodiment, the animal monitoring device has adjustable feet to level the animal monitoring device on an uneven surface. In many embodiments, the animal monitoring device can be slowly introduced to an animal to improve the incorporation of the animal monitoring device into the environment. For example, the animal monitoring device can be placed in the same room as the litterbox for a few days to allow the animal to acclimate to the presence of the animal monitoring device. Once the animal is comfortable with the presence of the animal monitoring device, the animal monitoring device can be turned down to allow the animal to become acclimated to the subtle sounds and lights the animal monitoring device may produce. Once the animal becomes acclimated to the animal monitoring device, a litter box can be placed on top of the animal monitoring device. Adding new litter to the litter box may encourage the animal to use the litter box.

In some embodiments, multiple user interfaces for configuring an animal health monitoring system are used. The user interfaces may include, a user interface for initiating an animal monitoring device setup process, a user interface for initiating a network setup process, a user interface for connecting via Bluetooth to an animal monitoring device during a setup process, a user interface for confirming connection to an animal monitoring device via Bluetooth during a setup process, a user interface connecting an animal monitoring device to a local area network, a user interface indicating that an animal monitoring device is ready to use, a user interface for physically positioning an animal monitoring device and litter box, and/or a user interface confirming the completion of a setup process.

A profile can be generated for each animal. This profile can be used to establish baseline characteristics of each animal and track the animal's behaviors and characteristics over time. This can include tracking weight, number and type of events, waste type, time of day of each event, and/or any other data as described herein.

In some embodiments, user interfaces for establishing an animal profile are used. Examples of user interfaces for establishing an animal profile include, a user interface of a start screen for an animal profile establishment process, a user interface of an introductory screen for an animal profile establishment, a user interface for entering an animal's name, a user interface for entering an animal's sex, a user interface for entering an animal's reproductive status, a user interface of an introductory screen explaining capturing an animal's current body condition, a user interface for examining an animal's rib, a user interface for examining an animal's profile, a user interface for examining an animal's waist, a user interface of an ending screen for an animal profile establishment process, a user interface for a type or brand of litter box being used including properties of the litter box, a user interface for a type of litter being used, and/or a user interface for a diet that the animal is being fed.

Every cat is unique and has unique behaviors. Animal health monitoring systems can utilize a variety of machine learning classifiers to track and distinguish between multiple animals without additional collars or gadgets. In some embodiments, information regarding particular events, such as an identification of which cat has used a litterbox, can be solicited from a user. This information can be used to confirm the identity of an animal associated with a particular event, which can be used to retrain the machine learning classifiers and improve the accuracy of future results. For example, if an animal's behavior and weight changes, the system can request confirmation of which animal is associated with an event so that the system continues to deliver the best available insight(s). In other embodiments, when animals in a multiple-animal environment have distinct weights, fewer event confirmations may be provided. In many embodiments, if the animals are approximately the same weight, placing each cat and animal monitoring device in a separate room can reduce the number of confirmation requests. In several embodiments, once the system has developed a unique profile for a particular animal (e.g. after a threshold number of confirmations), the frequency of future confirmation requests may decrease.

In some embodiments, user interfaces for labeling events may be used. The user interfaces may include a user interface showing a notification, a user interface requesting additional information for an event, a user interface requesting identification of an animal involved in an event, and a user interface showing the requested information associated with the event.

As described herein, characteristics of an animal and animal behaviors can be tracked and analyzed over time. The data can be analyzed over any time frame such as, but not limited to, 24 hours, 48 hours, one week, two weeks, one month, and the like. The analysis of animal behaviors and characteristics over time can be used to identify when changes in the animal's typical state occur, which can be indicators of adverse events requiring additional diagnosis or treatment.

In some embodiments user interfaces for tracking animal behaviors may be used. Examples of user interfaces for tracking animal behaviors include a user interface showing an animal's weight over a one week period, a user interface showing an animal's weight over a one week period, a user interface showing an animal's weight over a thirty day period, a user interface showing an animal's weight over a one year period, a user interface showing the number of times the animal's weight was measured on a particular day, a user interface showing the number of times the animal's weight was measured over a thirty day period, a user interface showing the number of times the animal's weight was measured over a one year period, a user interface showing the number of events at three different litter boxes over a one week period, a user interface showing the number of events at a litter box over a one week period, a user interface showing an indication of the types of events occurring at a litter box, a user interface showing the number of events at a litter box over a one week period, and/or a user interface showing the number of elimination events at a plurality of litter boxes. In one example, household, or other locations, can include a plurality of devices with litter boxes implementing embodiments of the present technology. The household may also include more than one animal that uses the devices. The data from the plurality of devices can be brought together to provide insights into each animal's behaviors at a household level.

As described herein, a variety of notifications can be provided indicating potential health concerns for an animal based on changes in the animal's behaviors. However, these indicated changes may be a false positive if the animal monitoring device has become misaligned or improperly calibrated. In these instances, the proper operation of the monitoring device should be confirmed before determining that additional attention should be paid to an animal to determine if any adverse health changes are occurring.

In some embodiments, user interfaces for expert advice notifications are used. The user interfaces may include a user interface showing a notification indicating a cat should be monitored due to weight loss, a user interface requesting confirmation that an animal monitoring device is correctly configured, a user interface requesting additional information regarding a cat's eating and drinking behaviors, a user interface requesting additional information regarding a cat's appearance, a user interface requesting additional information regarding a cat's elimination, and/or a user interface providing guidance to contact a veterinarian if changes in the cat's behaviors or condition are cause for concern.

Animal health monitoring systems track and record a variety of non-animal activities in addition to animal behaviors and activities as described herein. A variety of user interfaces can be used to provide insights into these animal and non-animal behaviors. For example, insights into typical animal behaviors can result in recommendations for ideal times to clean and/or maintain a litter box.

In some embodiments, user interfaces for animal behavior analytics are used. Examples of user interfaces for animal behavior analytics include, a user interface showing general behaviors of two animals over a time period, a user interface showing litterbox preferences of two animals over a time period, a user interface showing time-of-day behavioral patterns of two animals over a time period, a user interface comparing time-of day behavioral patterns of two animals and a user over a time period, and/or a user interface comparing time-of-day elimination behaviors of two animals and user maintenance events over a time period.

In accordance with FIG. 13, a method 1300 of monitoring the health of an animal, can include obtaining 1310 load data from an animal monitoring device including three or more load sensors associated with a platform carrying contained litter thereabove, wherein individual load sensors of the three or more load sensors are separated from one another and receive pressure input from the platform independent of one another, wherein the three or more load sensors individually sample loads at from 2.5 Hz to 110 Hz. In further detail, the method can include recognizing 1312 an animal behavior property associated with the animal if it is determined based on load data that the interaction with the contained litter was due to the animal interaction with the contained litter. The method can include classifying 1314 the animal behavior property into an animal classified event using a machine learning classifier.

In some examples, the method of claim 1300 includes the animal monitoring device communicating the load data, the animal classified event, or both from a data communicator to a client device over network. In some examples, the method 1300 further includes identifying a change in the animal classified event as compared to a previously recorded animal classified event or pattern of previously recorded animal classified events. In one example, the three or more load sensors individually sample loads at from 20 Hz to 110 Hz. In one example, the three or more load sensors individually sample loads at from 30 Hz to 80 Hz. In one example, the three or more load sensors individually sample loads of up to 10 kg. In one example, the animal monitoring device includes four load sensors. In one example, the platform has a rectangular shape and the four load sensors are each positioned at a different corner of the platform. In one example, the animal monitoring device has three load sensors and the platform is triangular in shape. In one example, the platform has a triangular shape and the three load sensors are each positioned at a different corner of the platform. In accordance with FIG. 14, a method 1400 of monitoring the health of an animal under the control of at least one processor, can include obtaining 1410 load data from an animal monitoring device including three or more load sensors associated with a platform carrying contained litter thereabove, wherein individual load sensors of the three or more load sensors are separated from one another and receive pressure input from the platform independent of one another. In further detail, the method can include recognizing 1412 an animal behavior property associated with the animal if it is determined based on load data that the interaction with the contained litter was due to the animal interaction with the contained litter. The method can further include classifying 1414 the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations when they occur.

In some examples, the method 1400 further includes the multiple discrete animal eliminations including both a urination event and a defecation event. The multiple discrete animal eliminations can include a first elimination and a second elimination, and wherein the animal classified events also include a first pre-elimination preceding the first elimination and a second pre-elimination preceding the second elimination. The animal classified events can further include a post-elimination that is occurring after the second elimination. The method 1400 can further include classifying using the phase separation algorithm establishing that there were not multiple discrete animal eliminations, either in the form of no animal elimination or only a single animal elimination during the animal interaction. The method 1400 can further include identifying a change in the animal classified events compared to previously recorded animal classified events. The method 1400 can further include correlating the change in the animal classified events with a physical, behavioral, or mental health issue associated with the animal.

In one example of the method 1400, the physical health issue is a feline disease selected from urinary disease, renal disease, diabetes, hyperthyroidism, idiopathic cystitis, digestive issues, or arthritis and the mental health issue is selected from anxiety, stress, or cognitive decline. In one example, identifying the change in animal classified events includes identifying a change in animal eliminations. In one example, the method 1400 further includes generating a notification indicating the change in the animal classified event, wherein the notification is generated after a parameter associated with the device event meets a threshold. In one example, the method further includes identifying the animal based on the load data, and distinguishing the animal from at least one other animal that interacts with the contained litter.

In one example of the method 1400, classifying the animal behavior property further comprises analyzing the load data from the three or more load sensors based on animal interaction with the contained litter to measure a distribution of weight of the animal, a location of an event, a duration of an event, a movement pattern, a force of entry, a force of exit, a volatility of the animal interaction, or a combination thereof. In one example of the method 1400, the animal behavior property further comprises analyzing the load data from the three or more load sensors to identify or measure the animal entering a litterbox carrying the contained litter, an amount of movement by the animal to select a particular elimination location, an amount of time to select a particular elimination location, an amount of time to prepare (e.g. digging) the elimination location, an amount of time spent covering the elimination, an amount of energy spent covering the elimination, a duration of the elimination, a total duration of the device event from entry to exit by the animal, a weight of the elimination, a motion of the animal during the elimination, a step/slope detection on a single load sensor during the elimination, the animal exiting the litter box positioned, one or more motions or impacts involving the litter box, or a combination thereof. In one example of the method 1400, classifying the animal behavior property further comprises analyzing load data from the three or more load sensors in both a time domain based on a time domain feature and a frequency domain based on a frequency domain feature based on animal interaction with the contained litter, wherein the time domain feature comprises a mean, a median, a standard deviation, a range, an autocorrelation, or a combination thereof, and wherein the time domain feature is created as an input or inputs for the machine learning classifier, and wherein the frequency domain features comprise a median, an energy, a power spectral density, or a combination thereof, and wherein the frequency domain feature is created as an input or inputs for the machine learning classifier. In one example of the method 1400, classifying the animal behavior property further comprises analyzing the load data from the three or more load sensors based on animal interaction with the contained litter to determine a movement pattern for the animal, the movement pattern comprising distance covered, speed, acceleration, direction of movement, alignment, distance from an entry point into a litter box positioned on the platform to the center of the litter box, elimination location, a resting location, a preferred quadrant of the litter box, or a combination thereof.

In one example, the method 1400 further includes generating an animal behavior model for an individual animal based on animal classified events unique to the individual animal. In one example, the three or more load sensors individually have a sampling rate from 2.5 Hz to 110 Hz. In one example, the three or more load sensors individually have a maximum load capacity up to 10 kg.

It will be appreciated that all of the disclosed methods and procedures described herein can be implemented using one or more computer programs, components, and/or program modules. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware and/or may be implemented in whole or in part in hardware components such as ASICs, FPGAs, DSPs, or any other similar devices. The instructions may be configured to be executed by one or more processors which, when executing the series of computer instructions, performs or facilitates the performance of all or part of the disclosed methods and procedures. As will be appreciated by one of skill in the art, the functionality of the program modules may be combined or distributed as desired in various aspects of the disclosure.

Although the present disclosure has been described in certain specific aspects, many additional modifications and variations would be apparent to those skilled in the art. In particular, any of the various processes described above can be performed in alternative sequences and/or in parallel (on the same or on different computing devices) in order to achieve similar results in a manner that is more appropriate to the requirements of a specific application. It is therefore to be understood that the present disclosure can be practiced otherwise than specifically described without departing from the scope and spirit of the present disclosure. Thus, aspects of the present disclosure should be considered in all respects as illustrative and not restrictive. It will be evident to the annotator skilled in the art to freely combine several or all of the aspects discussed here as deemed suitable for a specific application of the disclosure. Throughout this disclosure, terms like "advantageous", "exemplary" or "preferred" indicate elements or dimensions which are particularly suitable (but not essential) to the disclosure or an embodiment thereof, and may be modified wherever deemed suitable by the skilled annotator, except where expressly required. Accordingly, the scope of the present disclosure should be determined not by the embodiments illustrated, but by the appended claims and their equivalents.

What is claimed is:

1. A method of monitoring the health of an animal, comprising:
   obtaining load data from an animal monitoring device including three or more load sensors associated with a platform carrying contained litter thereabove, wherein individual load sensors of the three or more load sensors are separated from one another and receive pressure input from the platform independent of one another, wherein the three or more load sensors individually sample loads at from 2.5 Hz to 110 Hz;
   determining the load data is from an animal interaction with the animal monitoring device;
   recognizing an animal behavior property associated with the animal determined based on load data that the interaction with the contained litter was due to the animal interaction with the contained litter;
   employing normalization logic to analyze the load data for the purpose of classification; and
   classifying the animal behavior property into an animal classified event using a machine learning classifier including analyzing the load data via a phase separation algorithm, wherein the animal classified events include animal eliminations, and wherein the phase separation algorithm is capable of classifying multiple discrete animal eliminations.

2. The method of claim 1, wherein the animal monitoring device communicates the load data, the animal classified event, or both from a data communicator to a client device over network.

3. The method of claim 1, further comprising identifying a change in the animal classified event as compared to a previously recorded animal classified event or pattern of previously recorded animal classified events.

4. The method of claim 1, wherein the three or more load sensors individually sample loads at from 20 Hz to 110 Hz.

5. The method of claim 1, wherein the three or more load sensors individually sample loads at from 30 Hz to 80 Hz.

6. The method of claim 1, wherein the three or more load sensors individually sample loads of up to 10 kg.

7. The method of claim 1, wherein the animal monitoring device includes four load sensors.

8. The method of claim 1, wherein the animal monitoring device has three load sensors and the platform is triangular in shape.

9. The method of claim 1, wherein the multiple discrete animal eliminations include both a urination event and a defecation event.

10. The method of claim 1, wherein the multiple discrete animal eliminations include a first elimination and a second elimination, and wherein the animal classified events also include a first pre-elimination preceding the first elimination and a second elimination preceding the second elimination.

11. The method of claim 1, wherein classifying using the phase separation algorithm establishes that there were not multiple discrete animal eliminations, either in the form of no animal elimination or only a single animal elimination during the animal interaction.

12. The method of claim 1, further comprising identifying a change in the animal classified events compared to previously recorded animal classified events.

13. The method of claim 1, further comprising:
   identifying the animal based on the load data, and
   distinguishing the animal from at least one other animal that interacts with the contained litter.

14. The method of claim 1, wherein classifying the animal behavior property further comprises analyzing the load data from the three or more load sensors based on animal interaction with the contained litter to measure a distribution of weight of the animal, a location of an event, a duration of an event, a movement pattern, a force of entry, a force of exit, a volatility of the animal interaction, or a combination thereof.

15. The method of claim 1 wherein classifying the animal behavior property further comprises analyzing the load data from the three or more load sensors to identify or measure the animal entering a litterbox carrying the contained litter, an amount of movement by the animal to select a particular elimination location, an amount of time to select a particular elimination location, an amount of time spent covering the elimination, an amount of energy spent covering the elimination, a duration of the elimination, a total duration of the device event from entry to exit by the animal, a weight of the elimination, a motion of the animal during the elimination, a step/slope detection on a single load sensor during the elimination, the animal exiting the litter box positioned, one or more motions or impacts involving the litter box, or a combination thereof.

16. The method of claim 1, wherein classifying the animal behavior property further comprises analyzing load data from the three or more load sensors in both a time domain based on a time domain feature and a frequency domain based on a frequency domain feature based on animal interaction with the contained litter, wherein the time domain feature comprises a mean, a median, a standard deviation, a range, an autocorrelation, or a combination thereof, and wherein the time domain feature is created as an input or inputs for the machine learning classifier, and wherein the frequency domain features comprises a median, an energy, a power spectral density, or a combination thereof, and wherein the frequency domain feature is created as an input or inputs for the machine learning classifier.

17. The method of claim 1 wherein classifying the animal behavior property further comprises analyzing the load data from the three or more load sensors based on animal interaction with the contained litter to determine a movement pattern for the animal, the movement pattern comprising distance covered, speed, acceleration, direction of movement, alignment, distance from an entry point into a litter box positioned on the platform to the center of the litter box, elimination location, a resting location, a preferred quadrant of the litter box, or a combination thereof.

18. The method of claim 1, further comprising generating an animal behavior model for an individual animal based on animal classified events unique to the individual animal.

19. The method of claim 1, wherein the three or more load sensors individually have a maximum load capacity up to 10 kg.

20. The method of claim 7, wherein the platform has a rectangular shape and the four load sensors are each positioned at a different corner of the platform.

21. The method of claim 8, wherein the platform has a triangular shape and the three load sensors are each positioned at a different corner of the platform.

22. The method of claim 10, wherein the animal classified events further include a post-elimination that occurring after the second elimination.

23. The method of claim 12, further comprising correlating the change in the animal classified events with a physical, behavioral, or mental health issue associated with the animal.

24. The method of claim 23, wherein the physical health issue is a feline disease selected from urinary disease, renal disease, diabetes, idiopathic cystitis, digestive issues, or arthritis and the mental health issue is selected from anxiety, stress, or cognitive decline.

25. The method of claim 12, wherein identifying the change in animal classified events includes identifying a change in animal eliminations.

26. The method of claim 12, further comprises generating a notification indicating the change in the animal classified event, wherein the notification is generated after a parameter associated with the device event meets a threshold.

27. An animal monitoring system, comprising an animal monitoring device including:
   a platform configured to carry contained litter thereabove;
   three or more load sensors associated with the platform, wherein individual load sensors of the three or more load sensors are separated from one another and receive pressure input from the platform independent of one another, wherein the three or more load sensors individually sample loads at from 2.5 Hz to 110 Hz;
   a data communicator configured to independently communicate the load data from the three or more load sensors;
   a processor; and
   a memory storing instructions that, when executed by the processor, comprises:
      obtaining load data independently from the three or more load sensors,
      determining the load data is from an animal interaction with the animal monitoring device;
      recognizing an animal behavior property associated with the animal determined based on load data that an interaction with the platform was due to an animal interaction;
      employing normalization logic to analyze the load data for the purpose of classification; and
      classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations.

28. The animal monitoring system of claim 27, wherein the phase separation algorithm is capable of classifying a urination event separate from a defecation event.

29. The animal monitoring system of claim 27, wherein the phase separation algorithm is capable of establishing that there were not multiple discrete animal eliminations, either in the form of no animal elimination or only a single animal elimination during the animal interaction.

30. The animal monitoring system of claim 27, wherein the phase separation algorithm is capable of identifying the animal based on the load data, and distinguishing the animal from at least one other animal that interacts with the contained litter.

31. The animal monitoring system of claim 27, wherein the three or more load sensors individually sample loads at from 20 Hz to 110 Hz.

32. The animal monitoring system of claim 27, wherein the three or more load sensors individually sample loads at from 30 Hz to 80 Hz.

33. The animal monitoring system of claim 27, wherein the three or more load sensors individually sample loads of up to 10 kg.

34. The animal monitoring system of claim 27, wherein classifying the animal behavior property further comprises analyzing the load data from the three or more load sensors based on animal interaction with the contained litter to measure a distribution of weight of the animal, a location of an event, a duration of an event, a movement pattern, a force of entry, a force of exit, a volatility of the animal interaction, or a combination thereof.

35. The animal monitoring system of claim 28, wherein the phase separation algorithm is capable of classifying a first pre-elimination preceding the urination event and a second elimination preceding the defecation event.

36. The animal monitoring system of claim 28, wherein the phase separation algorithm is capable of classifying a post-elimination that occurring after both the urination event and the defecation event has occurred.

37. A non-transitory machine-readable storage medium having instructions embodied thereon, the instructions when executed cause a processor to perform a method of monitoring the health of an animal, comprising:
   obtaining load data from an animal monitoring device including three or more load sensors associated with a platform carrying contained litter thereabove, wherein individual load sensors of the three or more load sensors are separated from one another and receive pressure input from the platform independent of one another, wherein the three or more load sensors individually sample loads at from 2.5 Hz to 110 Hz;
   determining the load data is from an animal interaction with the animal monitoring device;
   recognizing an animal behavior property associated with the animal determined based on load data that the interaction with the contained litter was due to the animal interaction with the contained litter;
   employing normalization logic to analyze the load data for the purpose of classification; and
   classifying the animal behavior property into animal classified events using a machine learning classifier including analyzing the load data via a phase separation algorithm, wherein the animal classified events include animal eliminations, and wherein the phase separation algorithm is capable of classifying multiple discrete animal eliminations.

38. The non-transitory machine-readable storage medium of claim 37, wherein the phase separation algorithm is capable of classifying a urination event separate from a defecation event.

39. The non-transitory machine-readable storage medium of claim 37, wherein the phase separation algorithm is capable of establishing that there were not multiple discrete animal eliminations, either in the form of no animal elimination or only a single animal elimination during the animal interaction.

40. The non-transitory machine-readable storage medium of claim 37, wherein the phase separation algorithm is capable of identifying the animal based on the load data, and distinguishing the animal from at least one other animal that interacts with the contained litter.

41. The non-transitory machine-readable storage medium of claim 37, wherein the three or more load sensors individually sample loads at from 20 Hz to 110 Hz.

42. The non-transitory machine-readable storage medium of claim 37, wherein the three or more load sensors individually sample loads at from 30 Hz to 80 Hz.

43. The non-transitory machine-readable storage medium of claim 37, wherein the three or more load sensors individually sample loads of up to 10 kg.

44. The non-transitory machine-readable storage medium of claim 37, wherein classifying the animal behavior property further comprises analyzing the load data from the three or more load sensors based on animal interaction with the contained litter to measure a distribution of weight of the animal, a location of an event, a duration of an event, a movement pattern, a force of entry, a force of exit, a volatility of the animal interaction, or a combination thereof.

45. The non-transitory machine-readable storage medium of claim 38, wherein the phase separation algorithm is capable of classifying a first pre-elimination preceding the urination event and a second elimination preceding the defecation event.

46. The non-transitory machine-readable storage medium of claim 38, wherein the phase separation algorithm is capable of classifying a post-elimination that occurring after both the urination event and the defecation event has occurred.

* * * * *